United States Patent
Czerniecki et al.

(10) Patent No.: US 11,660,330 B2
(45) Date of Patent: May 30, 2023

(54) COMBINATION THERAPY WITH SEMAPHORIN-4D BLOCKADE (SEMA4D) AND DC1 THERAPY

(71) Applicants: H. Lee Moffitt Cancer Center and Research Institute, Inc., Tampa, FL (US); VACCINEX, INC., Rochester, NY (US)

(72) Inventors: Brian Czerniecki, Tampa, FL (US); Krithika N. Kodumudi, Tampa, FL (US); Elizabeth Evans, Bloomfield, NY (US)

(73) Assignees: H. Lee Moffitt Cancer Center and Research Institute, Inc., Tampa, FL (US); VACCINEX, INC., Rochester, NY (US)

( * ) Notice: Subject to any disclaimer, the term of this patent is extended or adjusted under 35 U.S.C. 154(b) by 190 days.

(21) Appl. No.: 16/906,713

(22) Filed: Jun. 19, 2020

(65) Prior Publication Data
US 2020/0397881 A1    Dec. 24, 2020

Related U.S. Application Data

(60) Provisional application No. 62/865,027, filed on Jun. 21, 2019.

(51) Int. Cl.
*A61K 39/00* (2006.01)
*A61K 9/00* (2006.01)
*A61K 39/395* (2006.01)

(52) U.S. Cl.
CPC .... *A61K 39/001102* (2018.08); *A61K 9/0019* (2013.01); *A61K 39/3955* (2013.01); *A61K 2039/5154* (2013.01)

(58) Field of Classification Search
None
See application file for complete search history.

(56) References Cited

U.S. PATENT DOCUMENTS

| | | |
|---|---|---|
| 3,610,795 A | 10/1971 | Antoine |
| 4,342,566 A | 8/1982 | Theofilopoulos et al. |
| 4,816,567 A | 3/1989 | Cabilly et al. |
| 5,565,332 A | 10/1996 | Hoogenboom et al. |
| 5,721,367 A | 2/1998 | Kay et al. |
| 5,804,440 A | 9/1998 | Burton et al. |
| 5,837,243 A | 11/1998 | Deo et al. |
| 5,939,598 A | 8/1999 | Kucherlapati et al. |
| 6,096,441 A | 8/2000 | Hauser et al. |
| 6,130,364 A | 10/2000 | Jakobovits et al. |

(Continued)

FOREIGN PATENT DOCUMENTS

| | | |
|---|---|---|
| WO | 9314125 A1 | 7/1993 |
| WO | 9429348 A2 | 12/1994 |
| WO | 2014209802 A1 | 12/2014 |

OTHER PUBLICATIONS

Tanyi et al. (Apr. 2018, Sci. Transl. Med. 10 (436) eaao5931, pp. 1-14).*

(Continued)

*Primary Examiner* — Elizabeth C. Kemmerer
(74) *Attorney, Agent, or Firm* — KDW Firm PLLC

(57) ABSTRACT

Disclosed are compositions and methods comprising the administration of pulsed dendritic cells and an immunoregulator molecule inhibitor for the treatment of cancer.

6 Claims, 26 Drawing Sheets
Specification includes a Sequence Listing.

(56) References Cited

U.S. PATENT DOCUMENTS

| | | | |
|---|---|---|---|
| 6,180,377 | B1 | 1/2001 | Morgan et al. |
| 8,496,938 | B2 | 7/2013 | Smith et al. |
| 8,816,058 | B2 | 8/2014 | Smith et al. |
| 9,243,068 | B2 | 1/2016 | Evans et al. |
| 9,605,055 | B2 | 3/2017 | Smith et al. |
| 9,676,840 | B2 | 6/2017 | Smith et al. |
| 2008/0219971 | A1 | 9/2008 | Smith et al. |
| 2010/0285036 | A1* | 11/2010 | Smith ............... A61P 37/02 435/69.6 |
| 2017/0216421 | A1* | 8/2017 | Czerniecki ............ A61K 45/06 |

OTHER PUBLICATIONS

Chiang et al. (2006, Cancer Immunol. Immunother. 55:1384-1385).*
Evans et al. (2015, Cancer Immunol. Res. 3(6):689-701).*
Schwartzberg et al. (2014, Clinical Breast Cancer 14(3):161-168).*
Song et al. (2010, J. Translational Immunology 162:75-83).*
web.expasy.org/abcd/ABCD_AL348; accessed Dec. 7, 2022.*
Fisher et al., 2016, mABs 8:1, pp. 150-162. T.*
De la Cruz et al., 2016, Immunotherapy 8(10):1219-1232.*
Bagshawe et al., "A cytotoxic agent can be generated selectively at cancer sited", Br. J. Cancer, 58:700-703, (1988).
Bagshawe, K.D., "The First Bagshawe Lecture. Towards generating cytotoxic agents at cancer sites", Br. J. Cancer, 60:275-281, (1989).
Battelli et al., "T lomphocyte killing by a xanthine-oxidase-containing immunotoxin", Cancer Immunol. Immunother., 35:421-425, (1992)—Abstract Submitted.
Brown et al., "Molecular and cellular mechanisms of receptor-mediated endocytosis", DNA and Cell Biology 10:6, 399-409 (1991)—Abstract Submitted.
Bruggemann et al., "Designer mice: the production of human antibody repertoires in transgenic animals", Year in Immunol. 7:33-40 (1993)—Abstract Submitted.
Cintolo JA, "Type I-polarized BRAF-pulsed dendritic cells induce antigen-specific CD8+ T cells that impact BRAF-mutant murine melanoma", Melanoma Res. Feb. 2016;26(1):1-11 (2016)—Abstract Submitted.
Clynes et al., "Inhibitory Fc receptors modulate in vivo cytoxicity against tumor targets", Nat Med. 6:443-446 (2000)—Abstract Submitted.
Datta et al., "Progressive loss of anit-HER2 CD4+ T-helper type 1 response in breast tumorigenesis and the potential for immune resotration", Oncoimmunology 4:10, e1022301 (2015).
Datta et al., Anti-HER2 CD4+ T-helper type 1 response is a novel immune correlate to pathologic response following neoadjuvant therapy in HER2-positive breast cancer, Breast Cancer Res. 17:71 (2015).
Evans et al., "Antibody Blockade of Semaphorin 4D Promoted Immune Infiltration into Tumor and Enhances Response to Other Immunomodulatory Therapies", Cancer Immunol. Res. 3(6):689-701 (2015).
Fracol et al., "Loss of Anti-HER-3 CD4+ T-Helper Type 1 Immunity Occurs in Breast Tumorigenesis and is Negatively Associated with Outcomes", Ann Surg Oncol 24:407-417 (2017). https://doi.org/10.1245/s10434-016-5584-6)—Abstract Submitted.
Herold et al., "Activation signals are delivered through two distinct epitopes of CD100, a unique 150 kDa human lymphocyte surface structure previously defined by BB18 mAb", Int. Immunol. 7(1):1-8 (1995)—Abstract Submitted.
Hughes et al., "Monoclonal Antibody Targeting of Liposomes to Mouse Lung in vivo1", Cancer Research 49:6214-6220 (1989).
Jakobovits et al., "Analysis of homozygous mutant chimeric mice: deletion of the immunoglobulin heavy-chain joining region blocks B-cell development and antibody production", Proc. Natl. Acad. Sci. 90:2551 2555 (1993)—Abstract Submitted.
Jakobovits et al., "Germ-line transmission and expression of a human-derived yeast artificial chromosome", Nature 362:255 258 (1993)—Abstract Submitted.
Jalali et al., "Induction of tumor-specific immunity by multi-epitope rat HER2/neu-derived peptides encapsulated in LPD nanoparticles", Nanomedicine 8:692-701 (2012).
Jones et al., "Replacing the complementarity-determining regions in a human antibody with those from a mouse", Nature 321:522 525 (1986)—Abstract Submitted.
Kohler et al., "Continuous cultures of fused cells secreting antibody of predefined specificity", Nature 256:495-497 (1975)—Abstract Submitted.
Litzinger et al., "Biodistribution and immunotargetability of ganglioside-stabilized dioleoylphosphatidylethanolamine liposomes", Biochimica et Biophysica Acta 1104(1):179-187, (1992)—Abstract Submitted.
Lowenfeld et al. "Dendritic Cell Vaccination Enhances Immune Responses and Induces Regression of HER2POS DCIS Independent of Route: Results of Randomized Selection Design Trial", Clin Cancer Res.23(12):2961-2971 (2017).
Pietersz et al., "Antibody Conjugates for the Treatment of Cancer", Immunol Rev 129:57-80, (1992).
Presta, LG, "Antibody engineering", Curr. Opin. Struct. Biol., 2(4):593 596 (1992)—Abstract Submitted.
Reichmann et al., "Reshaping human antibodies for therapy", Nature 332:323 327 (1988)—Abstract Submitted.
Roffler et al.,"Anti-neoplastic glucuronide prodrug treatment of human tumor cells targeted with a monoclonal antibody-enzyme conjugate", Biochem. Pharmacol, 42(10):2062-2065 (1991)—Abstract Submitted.
Rovero et al., "DNA Vaccination Against Rat Her-2/Nue p185 More Effectively Inhibits Carcinogenesis Than Transplantable Carcinomas In Transgenic BALB/c Mice", J. Immunol 165:5133-5142 (2000).
Senter et al., "Generation of 5-Fluorouracil from 5-Fluorocytosine by Monoclonal Antibody-Cytosine Deaminase Conjugates", Bioconjugate Chem 2:447-451, (1991)—p. 1 Included.
Senter et al., "Generation of Cytotoxic Agents by Tageted Enzymes", Bioconjugate Chem 4:3-9 (1993)—p. 1 Included.
Takai et al., "FcRγ chain deletion results in pleiotrophic effector cell defects", Cell. 76(3):519-529 (1994)—Abstract Included—Abstract Submitted.
Verhoeyen et al., "Reshaping hauman antibodies: grafting an antilysozyme activity", Science, 239(4847):1534 1536 (1988)—Abstract Included—Abstract Submitted.
Zhou et al. "Characterization of the Effects of Semaphorin 4D Signaling on Angiogenesis", Methods Mol Biol 1493:429-441 (2017).
Zoller MJ, "New recombinant DNA methodology for protein engineering", Curr Opin Biotech 3(4):348-354 (1992)—Abstract Included—Abstract Submitted.
Janos L. Tanyi et al., "Personalized cancer vaccine effectively mobilizes antitumor T cell immunity in ovarian cancer", Science Translational MEdicine vol. 10, No. 436, Apr. 11, 2018.
Rini et al., "Combination immunotherapy with prostatic acid phosphatase pulsed antigen-presenting cells (provenge) plus bevacizuam in patients with serologic progression of prostate cancer after definitive local therapy" Cancer, vol. 107, No. 1, Jan. 1, 2006, pp. 67-74.
Chiang: "Abstract LB-133: Vaccination with dendritic cells pulsed with autologous oxidized whole tumor lysate induced strong and long-lasting anti-tumor immunity in recurrent ovarian cancer patients." Cancer Research. Proceedings AACR 103rd Annual Meeting 2012, Apr. 1, 2012, pp. 1-4.
Evans, Elizabeth E., "Abstract PR10: Reprogramming myeloid cells in TME with pepinemab, first-in-class semaphorin 4D MAb, enhances combination immunotherapy." Cancer Research, Feb. 1, 2019, pp. 1-5.
Basu et al., "Multimodal approaches to improve immunotherapy in breast cancer", Immunotherapy, vol. 12, No. 3, Feb. 1, 2020, pp. 161-165.
International Search Report and Written Opinion for the International Patent Application No. PCT/US2020/038719, dated Sep. 22, 2020, 17 pages.

(56) References Cited

OTHER PUBLICATIONS

Disis, M L et al. "Generation of immunity to the HER-2/neu oncogenic protein in patients with breast and ovarian cancer using a peptide-based vaccine." Clinical cancer research : an official journal of the American Association for Cancer Research vol. 5,6 (1999): 1289-97. [abstract].

Markov, O V et al. "Antitumor Vaccines Based on Dendritic Cells: From Experiments using Animal Tumor Models to Clinical Trials." Acta naturae vol. 9,3 (2017): 27-38.

Zhong, Hua et al. "Low-dose paclitaxel prior to intratumoral dendritic cell vaccine modulates intratumoral cytokine network and lung cancer growth." Clinical cancer research : an official journal of the American Association for Cancer Research vol. 13,18 Pt 1 (2007): 5455-62. doi:10.1158/1078-0432.CCR-07-0517.

Kawakami, Yutaka et al. "Improvement of cancer immunotherapy by combining molecular targeted therapy." Frontiers in oncology vol. 3 136. May 28, 2013, doi:10.3389/fonc.2013.00136.

Chen, Ying et al. "Over-expression of semaphorin4D, hypoxia-inducible factor-1α and vascular endothelial growth factor is related to poor prognosis in ovarian epithelial cancer." International journal of molecular sciences vol. 13,10 13264-74. Oct. 16, 2012.

Long et al., "Epacadostat (E) plus pembrolizumab (P) versus pembrolizumab alone in patients (pts) with unresectable ar metastatic melanoma: Results of the phase 3 ECHO-301/KEYNOTE-252 study." Journal of Clinical Oncology—Meeting Abstract | 2018 ASCO Annual Meeting I.

Tallarida, R J. "Drug synergism: its detection and applications." The Journal of pharmacology and experimental therapeutics vol. 298,3 (2001): 865-72. Abstract.

\* cited by examiner

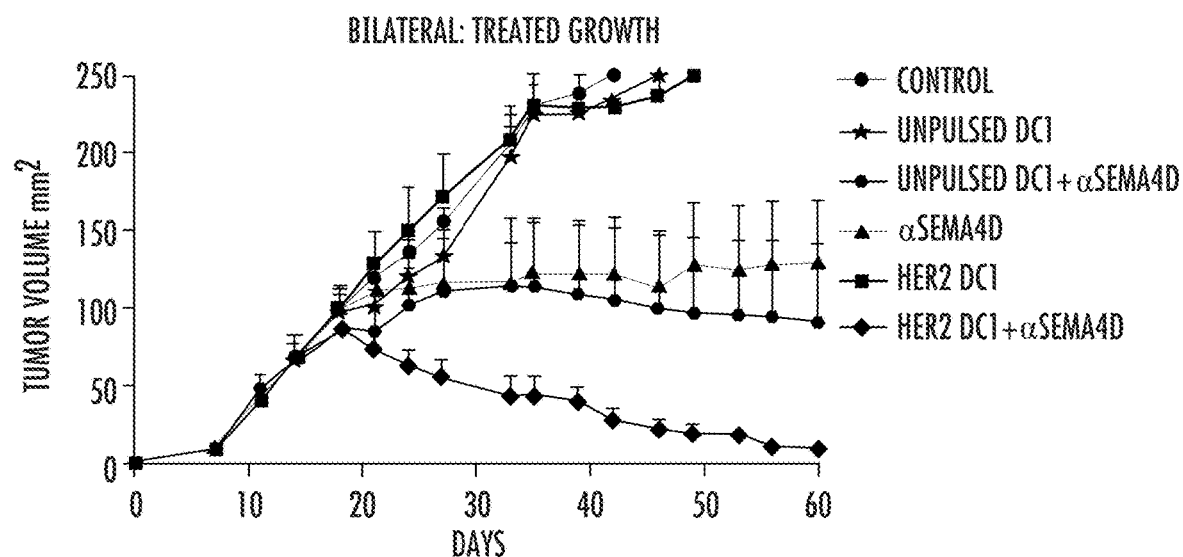
FIG. 3C1
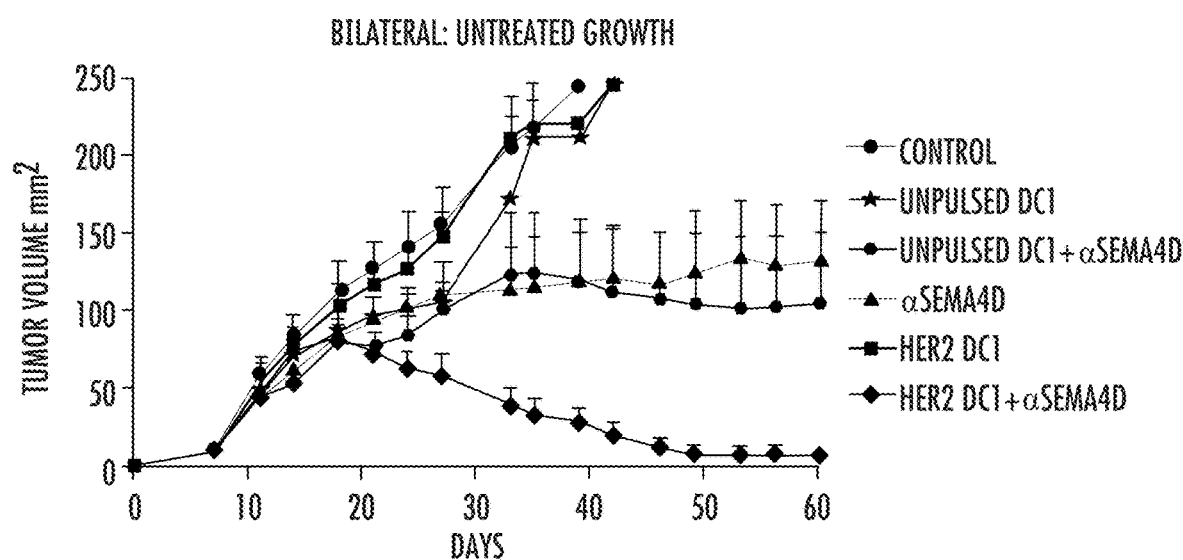
FIG. 3C2

| HER2 BREAST CANCER | SEMA4D CYTOKERATIN POSITIVE |
|---|---|
| DCIS | 8/15 |
| IBC | 7/13 |

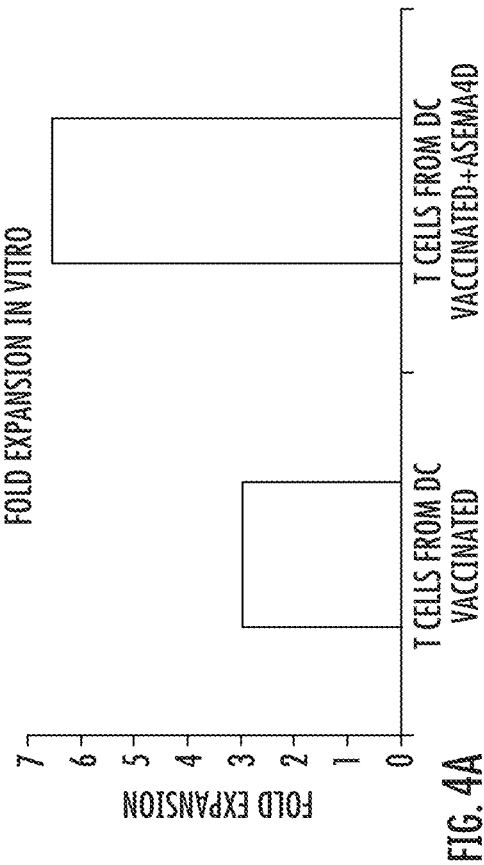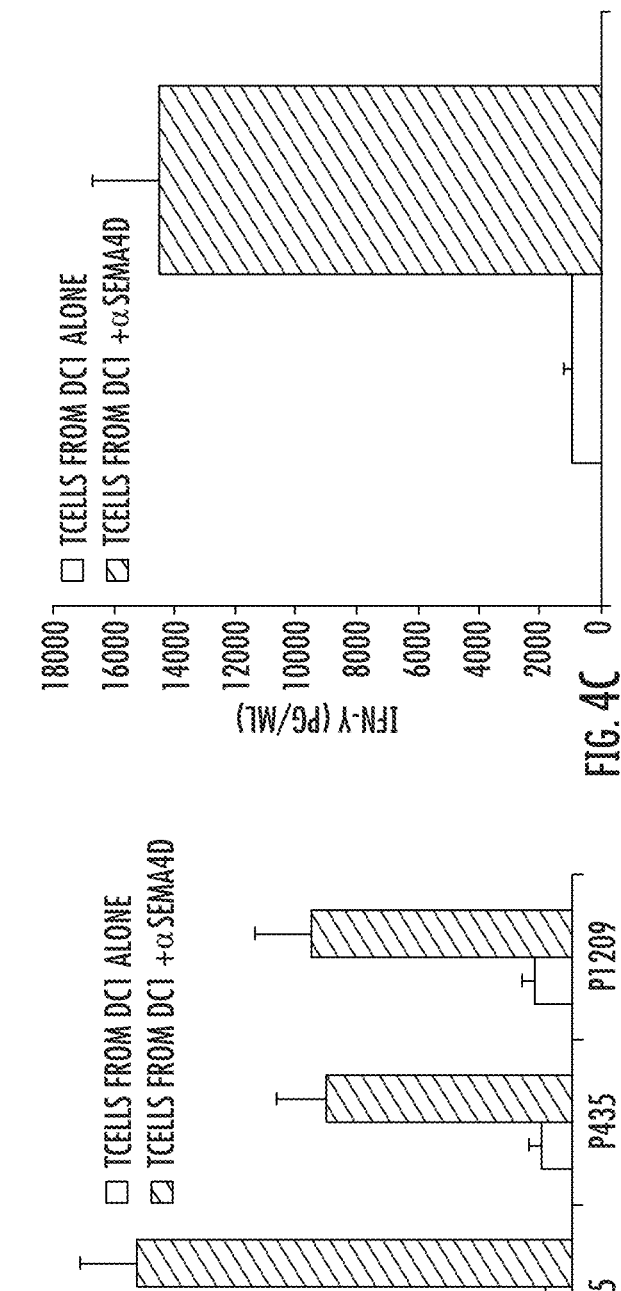

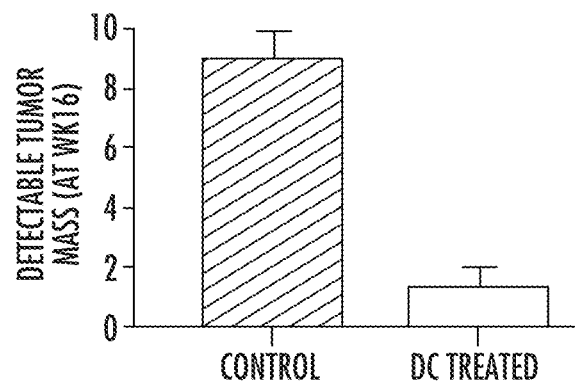
FIG. 6B
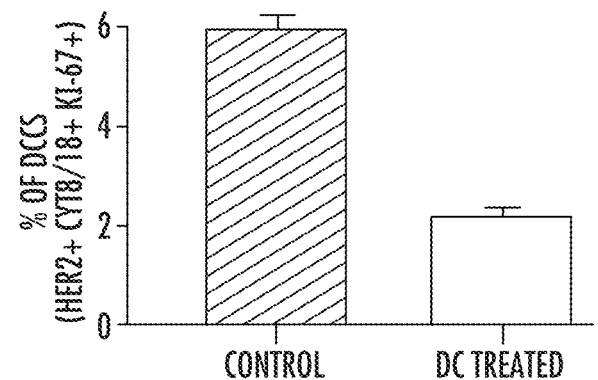
FIG. 6C
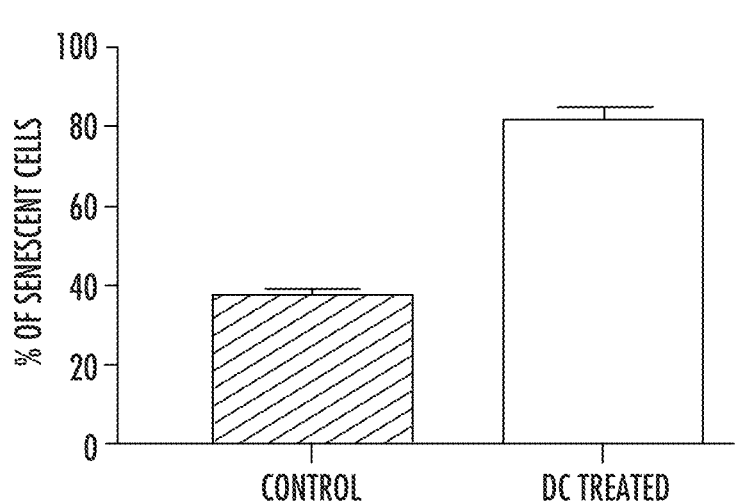
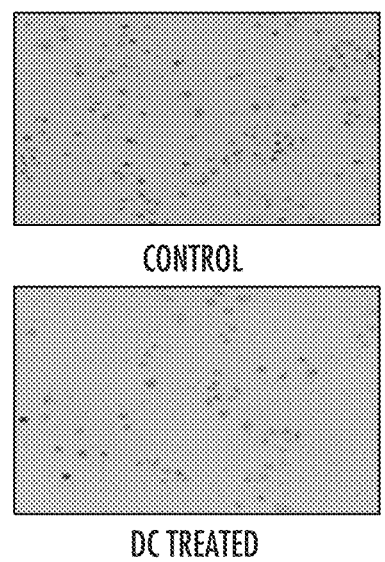
FIG. 6D

1) TNF-A (T)
2) IFN-G (I)
3) TRASTUZUMAB (TZm)
   + PERTUZUMAB (PER)
4) T+I + TZm PER

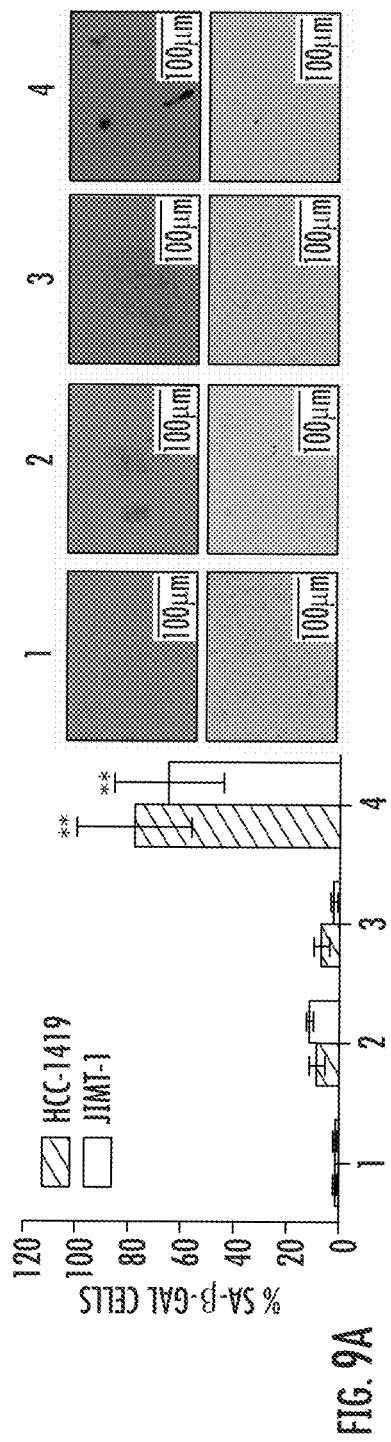
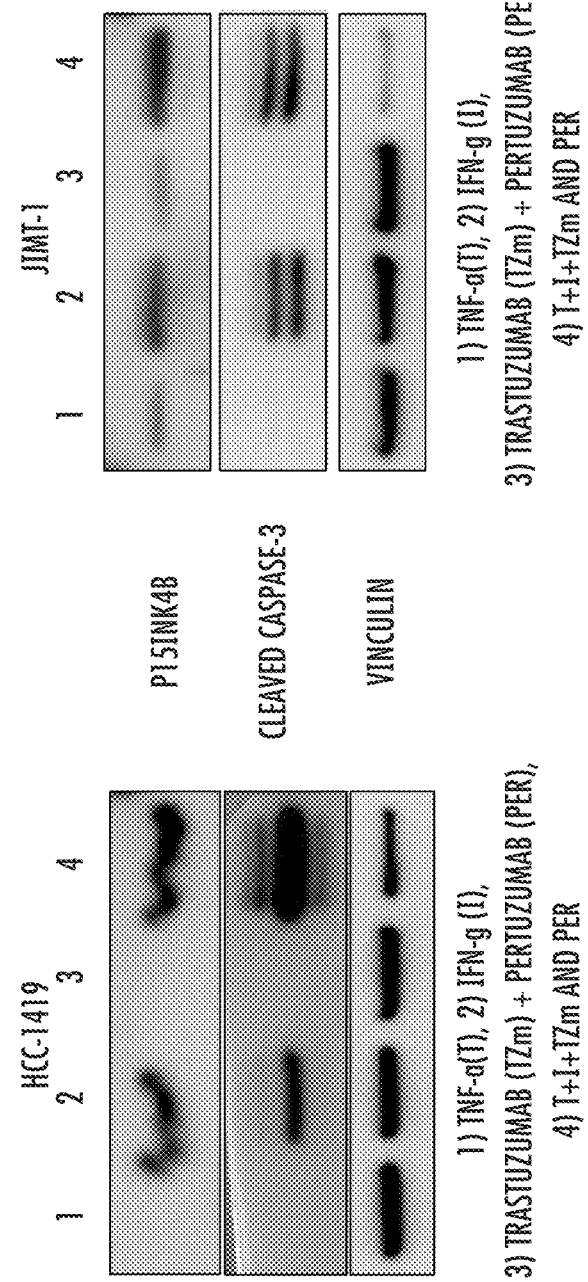
FIG. 9A
FIG. 9B
FIG. 9C

PHASE I RESPONSE DATA FOR THP-INF-γ
| BEST RESPONSE | | | |
|---|---|---|---|
| ARM | SEQUENCE NO. | BEST RESPONSE | BEST RESPONSE |
| 1 | 01 | STABLE DISEASE | 09/27/2017 |
| 1 | 03 | STABLE DISEASE | 10/17/2017 |
| 1 | 04 | PARTIAL RESPONSE | 10/25/2017 |
| 1 | 05 | STABLE DISEASE | 11/20/2017 |
| 1 | 06 | STABLE DISEASE | 10/19/2017 |
| 1 | 07 | STABLE DISEASE | 11/30/2017 |
| 1 | 08 | STABLE DISEASE | 01/24/2018 |
| 1 | 09 | PARTIAL RESPONSE | 02/16/2018 |
| 1 | 10 | PARTIAL RESPONSE | 02/15/2018 |
11/10/2017 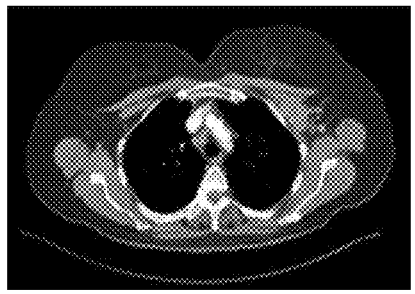 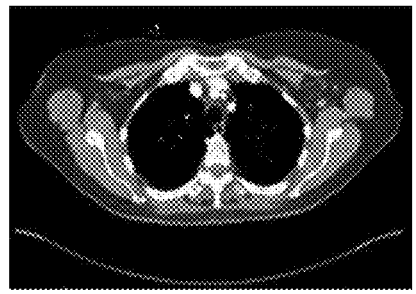 02/16/2018
FIG. 11

FIGURE X — PRE-VACCINE / POST-VACCINE

US 11,660,330 B2

COMBINATION THERAPY WITH SEMAPHORIN-4D BLOCKADE (SEMA4D) AND DC1 THERAPY

CROSS-REFERENCE TO RELATED APPLICATION

This is a non-provisional of pending U.S. provisional application Ser. No. 62/865,027, filed Jun. 21, 2019, the entirety of which application is incorporated by reference herein.

BACKGROUND

The aggressive features of various cancer types are mainly driven by oncodrivers such as HER2, HERS, EGFR, c-MET that are critically involved in cell growth, proliferation, survival and differentiation. Overexpression of these oncodrivers has associated with poor prognosis and a key player in tumor cell resistance to targeted therapies. Ductal carcinoma in situ (DCIS) is an early form of BC Stage 0 that impacts about 60,000 women in the US each year. These women are at elevated risk (25%) of having another BC event. Despite the excellent prognosis and 98% survival, there are some suggestions that women including those below age 40, African American women and those with estrogen receptor-negative ($ER^{neg}$) DCIS display a 7-15% chance of dying from subsequent BC probably because disseminated cancer cells (DCC) that escape prior to clinical detection of invasive breast cancer (IBC). Approximately 33-50% of high grade DCIS lesions express HER2 protein and another one third display modest HER2 expression. We have shown these women with HER2 DCIS have significantly greater likelihood of having an IBC component identified in their DCIS usually T1a/b (T1a are tumors under 5 mm T1b are tumors that are 5 mm-1 cm (see, e.g., American Joint Committee on Cancer (AJCC) Staging Manual-$8^{th}$ Edition, Amin, M. B., et al. Eds., Springer Nature (2017)) and increased risk of ipsilateral breast recurrence. In patients with T1b IBC the risk of subsequent mortality increases to 20-30% thus most of these women are offered adjuvant chemotherapy with trastuzumab to decrease risk. Although effective, even weekly paclitaxel and trastuzumab can result in neurologic, cardiac, cognitive as well as other morbidities. Many of these patients presenting with larger areas of DCIS mixed with T1a/b IBC and receive even more intense chemotherapy regimens like PTCH because the T stage of IBC can be difficult to discern. Many also require mastectomies because of the large areas of DCIS that do not always respond to neoadjuvant therapy. If these tumors are also estrogen receptor positive, patients are also treated with an additional 5 years of anti-estrogen further enhancing morbidity. To summarize, some HER2 DCIS patients are potentially undertreated and left with elevated risk of subsequent breast events even slightly increased mortality and the T1a/b patients can not infrequently be over-treated. Since existing targeted strategies are less effective, there is a need for attractive immunotherapeutic strategies.

SUMMARY

Disclosed are methods and compositions related to novel combination therapies comprising oncodriver pulsed dendritic cells and immunoregulator molecules inhibitors.

In one aspect, disclosed herein are anti-cancer combination therapies comprising at least one dendritic cell pulsed with an oncodriver (such as, for example, human epidermal growth factor receptor (HER) 2(HER2)) and at least one inhibitor of an immunoregulatory molecule (such as, for example, Semaphorin (SEMA) 4D (SEMA4D), or VEGF); wherein the immunoregulatory molecule being inhibited effects the vasculature of a tumor.

In one aspect, disclosed herein are methods of treating, preventing, reducing, and/or inhibiting a cancer (such as, for example, breast cancer (including triple negative breast cancer, metastatic breast cancer (MBC), ductal carcinoma in situ (DCIS), and invasive breast cancer (IBC)), melanoma, colorectal cancer, pancreatic cancer, prostate cancer, bladder cancer, ovarian cancer, and stomach cancer, and including primary and distant tumors) in a subject comprising administering the anti-cancer combination therapy of any preceding aspect. Thus, in one aspect, disclosed herein are methods of treating a cancer in a subject comprising administering to the subject at least one dendritic cell pulsed with an oncodriver (such as, for example, human epidermal growth factor receptor (HER) 2 (HER2)) and at least one inhibitor of an immunoregulatory molecule (such as, for example, Semaphorin (SEMA) 4D (SEMA4D), or VEGF); wherein the immunoregulatory molecule being inhibited effects the vasculature of a tumor.

Also disclosed are anti-cancer combination therapies methods treating, preventing, reducing, and/or inhibiting a cancer of any preceding aspect; wherein the at least one immunoregulatory molecule inhibitor is administered systemically and/or the oncodriver pulsed dendritic cell is administered intratumorally.

In one aspect, also disclosed herein are anti-cancer combination therapies methods treating, preventing, reducing, and/or inhibiting a cancer of any preceding aspect; wherein the oncodriver pulsed dendritic cell is activated with IL-12 prior to administration.

Also disclosed herein are anti-cancer combination therapies methods treating, preventing, reducing, and/or inhibiting a cancer of any preceding aspect; wherein the at least one immunoregulator molecule inhibitor comprises an antibody or functional fragment thereof which binds to SEMA4D (also referred to herein as CD100) such as, for example, the anti-SEMA4D antibodies Mab 67 or VX15/2503 (Pepinemab). See, e.g., U.S. Pat. No. 8,496,938, incorporated herein by reference.

In one aspect, also disclosed herein are anti-cancer combination therapies methods treating, preventing, reducing, and/or inhibiting a cancer of any preceding aspect; wherein the dendritic cells are removed from the subject and pulsed with oncodriver ex vivo.

Also disclosed herein are anti-cancer combination therapies methods treating, preventing, reducing, and/or inhibiting a cancer of any preceding aspect; wherein the pulsed dendritic cells are administered at least 1, 2, 3, 4, 5, 6, 7, 8, 9, 10, 11, 12, 18, 24, 30, 36 hours, 2, 3, 4, 5, 6, 7, 8, 9, 10, 11, 12, 13, 14, 21, 28, 30, 31, 45 days, 2, 3, 4, 5, or 6 months prior to administration of the at least one immunoregulatory molecule inhibitor; are administered concurrently with the at least one immunoregulatory molecule inhibitor; or wherein the at least one immunoregulatory molecule inhibitor is administered at least 1, 2, 3, 4, 5, 6, 7, 8, 9, 10, 11, 12, 18, 24, 30, 36 hours, 2, 3, 4, 5, 6, 7, 8, 9, 10, 11, 12, 13, 14, 21, 28, 30, 31, 45 days, 2, 3, 4, 5, or 6 months prior to administration of the pulsed dendritic cells.

In one aspect, disclosed herein are anti-cancer combination therapies methods treating, preventing, reducing, and/or inhibiting a cancer of any preceding aspect; wherein the at least one pulsed dendritic cell is administered at least 1, 2, 3, 4, 5, 6, 7, 8, 9, 10, 11, 12, 13, 14, 15, 16, 17, 18, 19, 20, 21, 22, 23, or 24 times per day or at least 1, 2, 3, 4, 5, 6, 7, 8, 9, 10, 11, 12, 13, or 14 times per week for at least 1, 2, 3, 4, 5, 6, 7, 8, 9, 10, 11, 12, 13, 14 days, 3, 4, 5, 6, 7, 8, 9, 10, 11, 12 weeks.

Also disclosed herein are anti-cancer combination therapies methods treating, preventing, reducing, and/or inhibiting a cancer of any preceding aspect; wherein the at least one immunoregulatory molecule inhibitor is administered at least 1, 2, 3, 4, 5, 6, 7, 8, 9, 10, 11, 12, 13, 14, 15, 16, 17, 18, 19, 20, 21, 22, 23, or 24 times per day or at least 1, 2, 3, 4, 5, 6, 7, 8, 9, 10, 11, 12, 13, or 14 times per week for at least 1, 2, 3, 4, 5, 6, 7, 8, 9, 10, 11, 12, 13, 14 days, 3, 4, 5, 6, 7, 8, 9, 10, 11, 12 weeks.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 1A shows that loss of HER-2 Th1 response with HER-2 positive disease progression; FIG. 1B shows that vaccine, but not standard therapy helps restore anti-HER-2 Th1 immunity; FIG. 1C shows that Th1 immunity to HER-2 predicts clinical response to standard therapy; and FIG. 1D shows that HER-2 Th1 responsivity predicts disease-free survival after standard therapy. Acronyms: DCIS: ductal carcinoma in situ; IBC: invasive breast cancer; Tx: treatment; pCR: pathologic complete response; ER: estrogen receptor; TNBC: triple-negative breast cancer.

FIG. 3A: SEMA4D expression in TUBO cells as measured by immunohistochemistry, compared to an IgG isotype control antibody; FIG. 3B: Intratumoral class II HER2 peptide pulsed DC1 intratumoral injection in combination with anti-SEMA4D antibody given intraperitoneally in single tumor model (FIG. 3B1) and survival curve (FIG. 3B2); FIG. 3C: Efficacy of intratumoral DC1 in combination with anti-SEMA4D in bilateral model (FIG. 3C1 and FIG. 3C2); TUBO bearing mice were treated with either with unpulsed or class II HER2 peptide pulsed activated DC1 alone or in combination with anti-SEMA4D antibody; FIG. 3D: IHC staining of SEMA4D in DCIS and IBC patients, the numbers indicate the number of patients with positive SEMA4D staining; FIG. 3E: Myeloid-derived suppressor cell (MDSC) infiltration per mg of tumor from treated with DC1 alone, anti-SEMA4D alone or in combination; FIG. 3F: CD4 T cell infiltration per mg of tumor; FIG. 3G: CD4 T cell infiltration (absolute number) in lymph node.

FIG. 4A, 4B, and 4C show that T cells from HER2-DC1+ aSema4D treated mice were superior in proliferation, function and specificity compared to T cells from HER2-DC1 alone vaccinated mice. FIG. 4A: Fold expansion after three weeks of in vitro CD4 T cell expansion. CD4+ T cells were isolated from isolated splenocytes from vaccinated mice using EASYSEP™ (Stemcell Technologies) and co-cultured with HER2 peptide pulsed DC1 followed by expansion with IL-2 and IL-7 for three weeks; FIG. 4B: Expanded T cells from DC1+ anti-SEMA4D treated mice were more antigen specific for the HER2/neu peptide antigens p5, p435, and p1209 compared to T cells from DC1 vaccinated mice; FIG. 4C: Cumulative IFN-γ response of expanded T cells.

FIG. 5A: Flow staining of DCC in bone marrow (BM) by cytokeratin 8/18 and HER2 expression; FIG. 5B: Immunofluorescence staining of HER2, cytokeratin and ki67; FIG. 5C: Detection of DCC in different organs of neu T mice.

FIGS. 6A, 6B, 6C, and 6D show HER2 peptide-DC1 vaccine prevents mammary tumor development, induce senescence and eliminate DCC in NeuT mice. FIG. 6A: Immunofluorescence staining of bone marrow DCC from control and DC1 vaccinated neu T mice; FIG. 6B: Detectable tumor mass in mammary glands using ultrasound; FIG. 6C: Percent DCC in bone marrow measured using flow cytometry; FIG. 6D: Detection of senescent cells using β-gal assay. Representative images after the β-gal staining.

FIG. 7A: 8 weeks old NeuT mice were treated with HER2 peptide pulsed DC1 vaccine (two injections per week for three weeks) or anti-SEMA4D antibody. On week 16, mice were sacrificed, and mammary glands were collected. The single cell suspension of mammary glands was prepared and stained for CD19 positive B cells then analyzed by flow cytometry. Increased levels of CDa19+ B cells were observed in DC1 vaccinated mice and anti-SEMA4D treated mice compared to untreated control; FIG. 7B: The bone marrow cells derived from the control and DC1 vaccinated NeuT mice were stained for CD4 and CD8 T cell markers and analyzed by flow cytometry. Increased numbers of CD4T cells and CD8 T cells were observed in the bone marrow of DC1 vaccinated NeuT mice compared to untreated control mice.

FIG. 8A: Dual blockade of HER2/HER3 in SK-BR-3 cells combined with Th1 cytokines TNF-α and IFN-γ enhance the number of senescent cells, higher SA-β-gal staining was observed in cells; FIG. 8B: SK-BR-3 cells untreated (1), treated with TNF-α and IFN-γ (2), or treated with trastuzumab (Herceptin, H (TZm)) and pertuzumab (Per) (3), or treated with TNF-α, IFN-γ and TZm and Per (4); FIG. 8C: Western blot analysis of SK-BR-3 cells treated with Th1 cytokines in combination with Tzm and Per induced Cyclin-dependent kinase 4 inhibitor B, also known as $p15^{INK4b}$ and cleaved caspase-3 expression (treatments numbered as in panel B); and FIG. 8D and FIG. 8E: Apoptosis by Annexin V/PI staining (treatments numbered as in panels D& E).

FIGS. 9A, 9B, and 9C show Th1 cytokines TNF-α and IFN-γ induces senescence and apoptosis in trastuzumab and pertuzumab resistant breast cancer cells. FIG. 9A: HCC-1419 and JIMT-1 cells; 1) untreated; 2) treated with TNF-α and IFN-γ; 3) treated with TZm and Per, or 4) treated with TNF-α, IFN-γ, Tzm, and Per. FIG. 9A. % of SA-β-gal-positive cells; FIG. 9B: Western blots analysis of $p15^{INKb}$ and cleaved caspase-3 expression of HCC-1419 post treatment; and FIG. 9C: Western blot analysis of JIMT-1 cells. Vinculin was used as a control.

FIG. 10A: SK-BR-3 cells co-cultured with CD4+ T-cells alone (CD4+ only (1)), CD4+ T-cells+HER2 peptide-pulsed immature dendritic cells (CD4+ IDC H (2)), CD4+ T-cells+HER2 peptide-pulsed mature dendritic cells (CD4+ DC H (3)), or CD4+ DC H with trastuzumab (Tzm) and pertuzumab (Per) (4), or CD4+ T-cells+irrelevant peptide-pulsed mature dendritic cells (BRAF (CD4+ DC B) (5); or survivin (CD4+ DC S)(6)), with Tzm and Per. FIG. 10B: Western blot analysis of tumor cells showed increase in p15$^{INK4b}$ and cleaved caspase-3 expression suggests induced senescence and apoptosis, respectively, when co-cultured with the DC H/CD4+ T-cells in presence of Tzm and Per, but not from DC B, DC S and iDC H groups. Vinculin was used as loading control FIG. 11 shows IFN-γ administered subcutaneously twice weekly with weekly Taxol and standard dose trastuzumab and pertuzumab in patients with first line metastatic breast cancer was safe and resulted in disease stabilization of partial responses.

FIG. 12A and FIG. 12B show areas of dense lymphocyte infiltrate; FIG. 12C and FIG. 12D show areas with little or no response.

FIG. 15A: Slope of the DCE-MRI curves calculated after iv administration of Gadavist (a gadolinium-based MRI contrast agent, 0.2 mmol/kg). Despite tumor volume, combo treatment shows a smaller slope which indicates less vessel leakage; FIG. 15B: DCE-MRI curves of TUBO tumors showing that combination therapy has smaller DCE curve. Data is represented as relative value (respect to the first point of the curve) to show a reliable comparison among the tumors.

FIG. 17A: mean tumor size (mm$^2$) in a murine Her2 TUBO breast cancer model over time following treatment with Her2DC1, anti-SEMA4D, HER2 DC1 plus anti-SEMA4D, or Control IgG. FIG. 17B: percent survival of Her2 TUBO tumor-bearing mice following treatment with Her2DC1, anti-SEMA4D, HER2 DC1 plus anti-SEMA4D, or Control IgG. FIG. 17C: mean tumor size (mm$^2$) in CD4-depleted Her2 TUBO tumor-bearing mice over time following treatment with Her2DC1, anti-SEMA4D, HER2 DC1 plus anti-SEMA4D, or no treatment. FIG. 17D: percent survival of CD4-depleted Her2 TUBO tumor-bearing mice following treatment with Her2DC1, anti-SEMA4D, HER2 DC1 plus anti-SEMA4D, or no treatment. FIG. 17E: tumor size (mm$^2$) in individual Her2 TUBO tumor-bearing mice over time following treatment with Her2DC1, anti-SEMA4D, HER2 DC1 plus anti-SEMA4D, or Control IgG. Complete tumor regressions are observed in control Balb/c mice following treatment with anti-SEMA4D and combination of anti-SEMA4D plus Her2DC1. FIG. 17F: tumor size (mm$^2$) in individual CD4-depleted Her2 TUBO tumor-bearing mice over time following treatment with Her2DC1, anti-SEMA4D, HER2 DC1 plus anti-SEMA4D, or Control IgG. (17E, F: Tumor growth curves for each mouse are shown; CR=complete tumor regression; tumor volume <50 mm2.) (*p<0.05, **p<0.01)

FIG. 18A: mean tumor size (mm$^2$) in BALB/C.129P2(B6)-Fcer1g$^{tm1Rav}$ N12 tumor-bearing mice treated with HER2DC, anti-SEMA4D, HER2DC plus anti-SEMA4D; or no treatment. FIG. 18B: percent survival of C.129P2(B6)-Fcer1g$^{tm1Rav}$ N12 tumor-bearing mice treated with HER2DC, anti-SEMA4D, HER2DC plus anti-SEMA4D; or no treatment. FIG. 18C: Tumor growth curves for each mouse are shown. No complete tumor regressions are observed in FcRγ-deficient mice. (*p<0.05, **p<0.01)

DETAILED DESCRIPTION

Figure 1A:
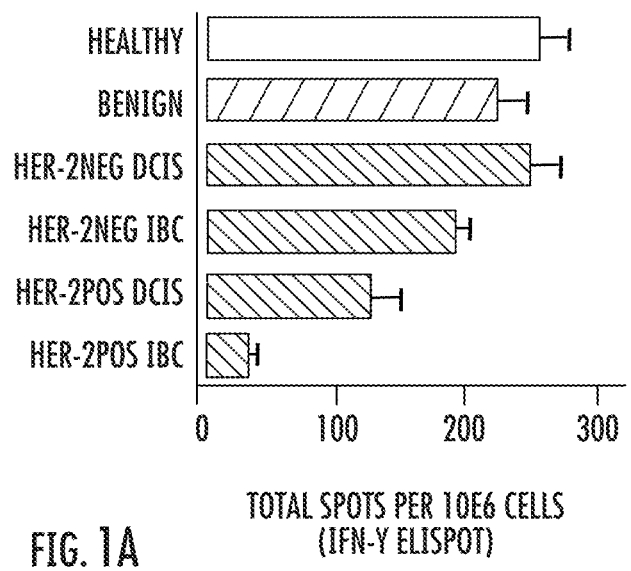
FIGS. 1A, 1B, 1C, and 1D show progressive loss of anti-oncodriver Th1 responses with advancing oncodriver-expressing breast disease, and association of anti-oncodriver immunity with improved clinical outcomes.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims that follow, reference will be made to a number of terms which shall be defined to have the following meanings:

"Optional" or "optionally" means that the subsequently described event or circumstance may or may not occur, and that the description includes instances where said event or circumstance occurs and instances where it does not.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

A "binding molecule" or "antigen binding molecule" (e.g., an antibody or antigen-binding fragment thereof) as provided herein refers in its broadest sense to a molecule that specifically binds an antigenic determinant In one embodiment, the binding molecule specifically binds to an immunoregulator molecule (such as for example, a transmembrane SEMA4D (CD100) polypeptide of about 150 kDa or a soluble SEMA4D polypeptide of about 120 kDa). In another embodiment, a binding molecule is an antibody or an antigen binding fragment thereof, e.g., MAb 67 or pepinemab.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular immunoregulator molecule inhibitor or oncodriver pulsed dendritic cell is disclosed and discussed and a number of modifications that can be made to a number of molecules including the immunoregulator molecule inhibitor or oncodriver pulsed dendritic cell are discussed, specifically contemplated is each and every combination and permutation of immunoregulator molecule inhibitor or oncodriver pulsed dendritic cell and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Patients presenting with DCIS in general have excellent prognosis however those presenting at age <40, African American females, and $ER^{neg}$ DCIS have modestly increased risk of dying of subsequent BC that neither surgery nor radiation appears to prevent. A second problem is that many young patients also present with larger regions of HER2 expressing DCIS that contains areas of T1a/T1b invasion. These patients are typically either treated with mastectomy because of the size of area of calcifications or treated with strong neoadjuvant chemotherapy regimens of carboplatin, taxotere with trastuzumab and pertuzumab (PTCH) or taxol and trastuzumab (TH) with good survival but to suffer the long term consequences of extensive surgery, radiation and chemotherapy. In a day of personalized medicine these patients need more personalized effective therapy that both reduces the odds of subsequent BC mortality and at the same time reduces the overtreatment they receive from chemotherapy, a year of trastuzumab, radiation and often mastectomies. Patients with metastatic breast cancer (MBC) are in desperate need of new immunotherapies to reduce mortality especially those that become resistant to targeted therapies.

HER-2/neu over-expression plays a critical role in breast cancer (BC) development and its expression in ductal carcinoma in situ (DCIS) is associated with development of invasive BC (IBC). There is a progressive loss of the systemic anti-HER2 Th1 immune response in HER2 positive DCIS and invasive BC patients. Administration of class II HER2 peptide-pulsed Type I polarized dendritic cell vaccine (HER2-DC1) partially restored anti-HER2 Th1 immune responses with about 30% pathologic complete response rate (pCR) in DCIS. There is opportunity to improve the immune response and clinical activity in patients with early HER2 BC. Semaphorin 4D (SEMA4D) is a family of soluble and transmembrane proteins that are essential for tissue and organ development and are involved in immune regulation. Overexpression of SEMA4D correlates with poor prognosis and tumor progression in various cancers. In this study, a murine anti-SEMA4D monoclonal antibody (provided by Vaccinex) in combination with DC1 vaccine was investigated to enhance anti-tumor immune response in a preclinical model of HER2 positive TUBO breast cancer.

In one aspect, disclosed herein are anti-cancer combination therapies comprising at least one dendritic cell pulsed with an oncodriver (such as, for example, human epidermal growth factor receptor HER2, and at least one inhibitor of an immunoregulatory molecule (such as, for example, Semaphorin (SEMA) 4D (SEMA4D), or VEGF). In certain nonlimiting aspects, the immunoregulatory molecule being inhibited can affect the vasculature of a tumor.

It is understood and herein contemplated that the disclosed anti-cancer combination therapies can be used to treat, prevent, reduce, and/or inhibit any disease where uncontrolled cellular proliferation occurs such as cancers including primary and distant tumors. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer (including triple negative breast cancer, metastatic breast cancer (MBC), ductal carcinoma in situ (DCIS), and invasive breast cancer (IBC)), and epithelial cancer, renal cancer, genitourinary cancer, pulmonary cancer, esophageal carcinoma, head and neck carcinoma, large bowel cancer, hematopoietic cancers; testicular cancer; colorectal cancer, prostatic cancer, or pancreatic cancer. Thus, in one aspect, disclosed herein are methods of treating, preventing, reducing, and/or inhibiting a cancer (such as, for example, breast cancer (including triple negative breast cancer, metastatic breast cancer (MBC), ductal carcinoma in situ (DCIS), and invasive breast cancer (IBC)), melanoma, colorectal cancer, pancreatic cancer, and prostate cancer and including primary and distant tumors) in a subject comprising administering the anti-cancer combination therapy of any preceding aspect. For example, disclosed herein are methods of treating, preventing, reducing, and/or inhibiting a cancer in a subject comprising administering to the subject at least one dendritic cell pulsed with an oncodriver (such as, for example, human epidermal growth factor receptor (HER) HER2, and at least one inhibitor of an immunoregulatory molecule (such as, for example, Semaphorin (SEMA) 4D (SEMA4D), or VEGF). In certain nonlimiting aspects, the immunoregulatory molecule being inhibited can affect the vasculature of a tumor.

In one aspect, it is understood that the disclosed methods and anti-cancer combination therapies comprise inhibitor of an immunoregulatory molecules that have both an immunoregulatory effect, and in certain nonlimiting aspects can also affect the vasculature of a tumor. It is understood and herein contemplated that said inhibitors can comprise any small molecule, peptide, protein, antibody (including any functional fragments of an antibody or other binding molecule), and/or functional nucleic acid (siRNA, RNA, aptamer) that inhibits the immunoregulatory and/or vascular activity of the immunoregulatory molecule. In one aspect, the inhibitor of an immunoregulatory molecule comprises the SEMA4D inhibitor pepinemab (an anti-SEMA4D antibody)

Antibodies

Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with an immunoregulatory molecule (such as, for example, Semaphorin (SEMA) 4D (SEMA4D), or VEGF) such that the immunoregulator molecule is inhibited from its immunoregulatory activity and/or its effects on the vasculature of a tumor. The antibodies can be tested for their desired activity using the in vitro assays described herein, or by analogous methods, after which in vivo therapeutic and/or prophylactic activities can be tested according to known clinical testing methods. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulin s can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

In certain antibodies, or antigen-binding fragments, variants, or derivatives thereof disclosed herein (such as, for example the anti-SEMA4D antibody pepinemab), the heavy chain portions of one polypeptide chain of a multimer are identical to those on a second polypeptide chain of the multimer. Alternatively, heavy chain portion-containing monomers are not identical. For example, each monomer may comprise a different target binding site, forming, for example, a bispecific antibody.

The heavy chain portions of a binding molecule for use in the diagnostic and treatment methods disclosed herein may be derived from different immunoglobulin molecules. For example, a heavy chain portion of a polypeptide may comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-SEMA4D antibodies, or antigen-binding fragments, variants, or derivatives thereof disclosed herein can be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant" A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-SEMA4D antibodies may contain a sequence of at least 4, at least 5, at least 6, at least 7, more preferably at least 8, at least 9, at least 10, at least 15, at least 20, at least 25, or between about 15 to about 30 contiguous or non-contiguous amino acids of SEMA4D.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, and fragments, such as F(ab')2, Fab', Fab, Fd, Fv, scFv, disulfide-linked Fvs (sdFv), fragments comprising either or both $V_H$ or $V_L$ domain, and the like, including hybrid fragments. Thus, fragments of the antibodies that retain the ability to bind their specific antigens are provided. For example, fragments of antibodies which maintain immunoregulatory molecule (such as, for example, Semaphorin (SEMA) 4D (SEMA4D), or VEGF) binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual.* Cold Spring Harbor Publications, New York, (1988)).

Also included within the meaning of "antibody or fragments thereof" are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human Antibodies

The disclosed human antibodies can be prepared using any technique. The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an sFv, Fv, Fab, Fab', F(ab')2, or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Anti-SEMA4D Antibodies

In one aspect, the inhibitor of an immunoregulatory molecule can be the SEMA4D inhibitor pepinemab (an anti-SEMA4D antibody) such as those described in U.S. Pat. Nos. 8,496,938, 8,816,058, 9,605,055, and 9,676,840, patents which are incorporated herein by reference for their teachings of anti-SEMA4D (anti-DC100) antibodies. Anti-SEMA4D monoclonal antibodies have been developed to neutralize SEMA4D, including MAb 67, MAb 2503, and MAb 76.

Antibodies that bind SEMA4D have been described the art. See, for example, US Publ. No. 2008/0219971 A1, International Patent Application WO 93/14125 and Herold et al., *Int. Immunol.* 7(1): 1-8 (1995), each of which is herein incorporated in its entirety by reference.

Anti-SEMA4D antibodies or antigen-binding fragments, variants, or derivatives thereof can include, e.g., MAb 2503, MAb 67, or MAb 76. In certain embodiments the anti-SEMA4D antibodies bind human, murine, or both human and murine SEMA4D. In other embodiments, the anti-SEMA4D antibodies block SEMA4D binding to its receptor, e.g., Plexin-B1 or Plexin-B2.

It is understood and herein contemplated that the disclosed anti-cancer combination therapies and methods of treating, inhibiting, reducing, and/or preventing a cancer using said anti-cancer combination therapies can comprise more than one immunoregulator molecule inhibitor and more than one population of pulsed dendritic cells with each population of pulsed dendritic cells being pulsed with the same or different oncodrivers.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

In one aspect, it is understood and herein contemplated that the pulsed dendritic cells can be activated prior to administration as well as prior to being pulsed with the oncodriver. Activation of the dendritic cells (DC1) can be achieved by contacting the cells with IFN-$\gamma$, TNF$\alpha$, CD40, IL21, and/or IL-12. In one aspect, it is further understood that the subject's own dendritic cells can be removed and pulsed ex vivo and transferred back to the subject for use in the disclosed anti-cancer combination therapies for treating, preventing, reducing, and/or inhibiting a cancer.

It is understood and herein contemplated that the disclosed anti-cancer combination therapies can be administered via any route determined to be appropriate by the attending physician. Administration" to a subject includes any route of introducing or delivering to a subject an agent either locally and/or systemically. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intratumoral, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another. In one aspect, disclosed herein are anti-cancer combination therapies methods treating, preventing, reducing, and/or inhibiting a cancer of any preceding aspect; wherein the at least one immunoregulatory molecule inhibitor is administered systemically and/or the oncodriver pulsed dendritic cell is administered intratumorally.

It is understood and herein contemplated that while a single administration of the components of the disclosed anti-cancer combination therapies (i.e., the pulsed dendritic cells and/or the immunoregulator molecule inhibitor) would be ideal, not every patient will respond in the same manner Thus, in one aspect, disclosed herein are anti-cancer combination therapies methods treating, preventing, reducing, and/or inhibiting a cancer; wherein the at least one pulsed dendritic cell is administered at least 1, 2, 3, 4, 5, 6, 7, 8, 9, 10, 11, 12, 13, 14, 15, 16, 17, 18, 19, 20, 21, 22, 23, or 24 times per day or at least 1, 2, 3, 4, 5, 6, 7, 8, 9, 10, 11, 12, 13, or 14 times per week for at least 1, 2, 3, 4, 5, 6, 7, 8, 9, 10, 11, 12, 13, 14 days, 3, 4, 5, 6, 7, 8, 9, 10, 11, 12 weeks. Also disclosed herein are anti-cancer combination therapies methods treating, preventing, reducing, and/or inhibiting a cancer of any preceding aspect; wherein the at least one immunoregulatory molecule inhibitor is administered at least 1, 2, 3, 4, 5, 6, 7, 8, 9, 10, 11, 12, 13, 14, 15, 16, 17, 18, 19, 20, 21, 22, 23, or 24 times per day or at least 1, 2, 3, 4, 5, 6, 7, 8, 9, 10, 11, 12, or 14 times per week for at least 1, 2, 3, 4, 5, 6, 7, 8, 9, 10, 11, 12, 13, 14 days, 3, 4, 5, 6, 7, 8, 9, 10, 11, 12 weeks. It is further understood and herein contemplated that the order and duration of the administered components can vary as appropriate for the subject being treated. In one aspect, disclosed herein are anti-cancer combination therapies methods treating, preventing, reducing, and/or inhibiting a cancer; wherein the pulsed dendritic cells are administered at least 1, 2, 3, 4, 5, 6, 7, 8, 9, 10, 11, 12, 18, 24, 30, 36 hours, 2, 3, 4, 5, 6, 7, 8, 9, 10, 11, 12, 13, 14, 21, 28, 30, 31, 45 days, 2, 3, 4, 5, or 6 months prior to administration of the at least one immunoregulatory molecule inhibitor; are administered concurrently with the at least one immunoregulatory molecule inhibitor; or wherein the at least one immunoregulatory molecule inhibitor is administered at least 1, 2, 3, 4, 5, 6, 7, 8, 9, 10, 11, 12, 18, 24, 30, 36 hours, 2, 3, 4, 5, 6, 7, 8, 9, 10, 11, 12, 13, 14, 21, 28, 30, 31, 45 days, 2, 3, 4, 5, or 6 months prior to administration of the pulsed dendritic cells.

As noted above, it is intended herein that the disclosed methods of treating, inhibiting, reducing, and/or preventing cancer can augmented with any therapeutic treatment of a cancer including, but not limited surgical, radiological, and/or pharmaceutical treatments of a cancer. As used herein, "surgical treatment" refers to tumor resection of the tumor by any means known in the art. Similarly, "pharmaceutical treatment" refers to the administration of any anti-cancer agent known in the art including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane),Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Also contemplated herein are chemotherapeutics that are PD1/PDL1 blockade inhibitors (such as, for example, lambrolizumab, nivolumab, pembrolizumab, pidilizumab, BMS-936559, Atezolizumab, Durvalumab, or Avelumab).

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Pharmaceutically Acceptable Carriers

The compositions, including antibodies, can be used therapeutically in combination with a pharmaceutically acceptable carrier.

Suitable carriers and their formulations are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines Therapeutic Uses Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Anti-oncodriver Th1 Responses in Breast Cancer

Most breast tumors express oncodrivers including HER2, EGFR (ER+ and TNBC), C-MET (TNBC) and HERS (ER+, HER2, and TNBC). These oncodrivers or downstream pathways are often targeted by many therapeutics and patients with metastatic breast cancer (MBC) are often treated with targeted agents such as anti-estrogens, CDK4/6 inhibitors, HER2 directed therapies and AKT inhibitors. Most of these patients, however, become resistant to therapies or stop responding and progress. Thus, these patients are in need of additional therapies. Checkpoint therapies have shown promising but limited effectiveness in MBC so identifying effective new immunotherapies that may be combined with targeted agents to make them more effective in MBC would be highly desirable. Oncodrivers may be critical appropriate targets of the immune response as indicated by the data below.

Evidence for Loss of Anti-Oncodriver Th1 Response During Tumorigenesis

Figure 1B:
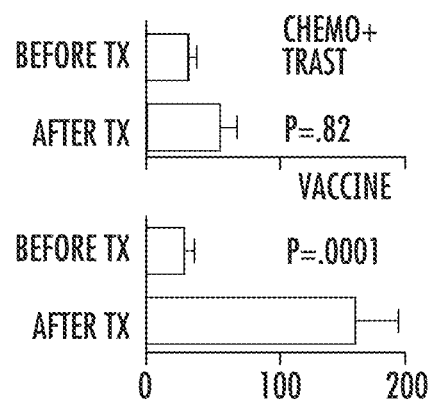
Figure 1C:
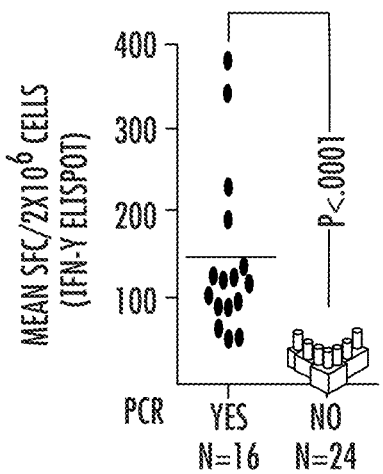
Figure 1D:
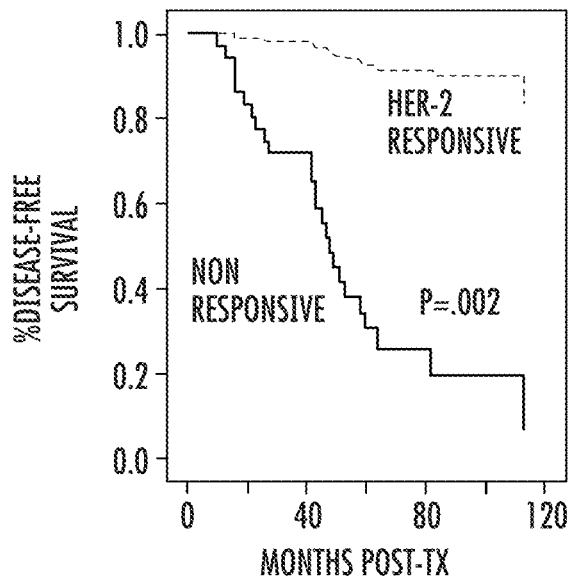

Healthy adult women possess unusually high, pre-existing Th1 immunity against HER2 (FIG. 1A and 1C, see, e.g., Dana J, et al., Oncoimmunology. 2015;4:e1022301; Dana J, et al., *Breast Cancer Res*. 2015;17:71; and Fracol, M., et al., *Ann Surg Oncol* (2017) 24: 407. https://doi.org/10.1245/s10434-016-5584-6) in the peripheral blood. These Tbet$^{pos}$ Th1 cells, however, are progressively lost during tumorigenesis. This deficit is first detectable at the ductal carcinoma in situ (DCIS) stage and becomes profoundly suppressed by stage I invasive breast cancer (IBC) stage (FIG. 1A, 1C, and 1D). There is no such loss of HER2 Th1 immune responses during HER2$^{neg}$ tumorigenesis (FIG. 1A), neither are there losses of responsiveness against other (non-tumor) control antigens (data not shown), indicating this suppression is antigen-selective and not a product of global anergy. Standard therapy of surgery, radiation, and chemotherapy with trastuzumab do not routinely correct this anti-HER2 Th1 loss, but vaccination with HER2-pulsed type I dendritic cells (DC1) can dramatically increase peripheral anti-HER2 CD4 Th1, indicating this is not a fixed deficit, but instead one that can be corrected by appropriate immunization (FIG. 1B). It is unclear whether the diminishment in peripheral blood CD4 Th1 signals a true loss of cells or represents a shift from central circulation to peripheral sites.

The Anti-HER2 Th1 Response Correlates with Clinical Outcomes

HER2$^{pos}$ IBC patients achieving a pathological complete response (pCR) to neoadjuvant chemotherapy (NAC) demonstrate improved survival while those with residual disease at the time of surgery demonstrate increased risk of recurrence. Although invasive HER2$^{pos}$ IBC patients show depressed anti-HER2 Th1 immunity as a group, some individuals are profoundly suppressed while others retain moderate responsiveness. Those patients that regain or partially retain anti-HER2 Th1 demonstrate higher pCR rate to neoadjuvant chemo/trastuzumab therapy, while those with residual disease display the lowest anti-HER2 CD4 Th1 responses (FIG. 1D). Shown is the loss of repertoire but there is also significant difference in overall and cumulative responses. The loss of anti-oncodriver CD4 immune response represents a decrease in interferon gamma (IFN-γ) production in the Tbet$^{pos}$ Th1 population and not GATA 3$^{pos}$ Th2 population, indicating the Th1 immune response may be critical to mediating anti-oncodriver BC responses. Indeed, elevated immune gene expression in the tumor is associated with improved outcomes. We have also investigated the relationship between anti-HER2 immunity and disease-free survival (DFS). Patients with the recurrence and reduced DFS display the most diminished anti-HER2 Th1 immune response (FIG. 1F) while those with retained peripheral anti-HER2 Th1 response have substantially greater DFS (FIG. 1F). This deficit in the peripheral CD4Th1 may reflect immunologic activity away from the periphery or true loss of tolerized or exhausted response.

Figure 2A:
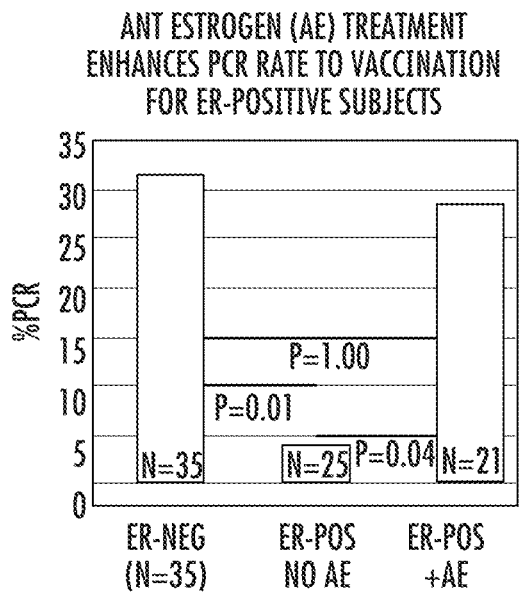
FIGS. 2A, 2B, and 2C show short-course anti-estrogen therapy concurrent with DC1 vaccination improves pCR rate (FIG. 2A) and anti-HER2 Th1 immunity (FIG. 2B) for subjects with hormone-dependent (ER-positive) disease, and that pathologic complete response (pCR) predicts long-term freedom from subsequent breast events (SBE) for all vaccinated subjects (FIG. 2C).
Figure 2B:
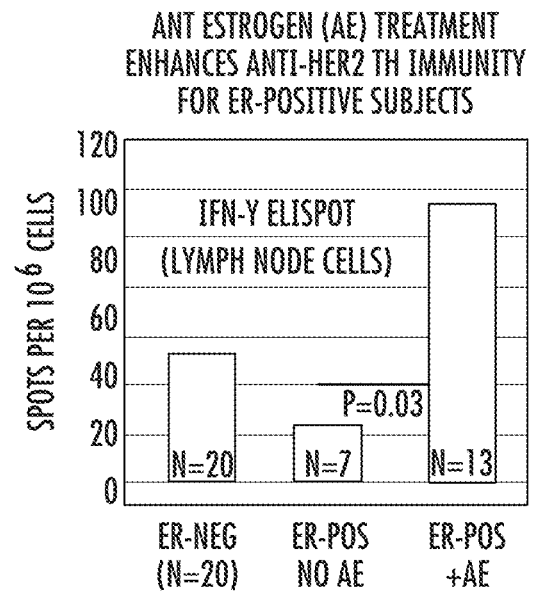
Figure 2C:
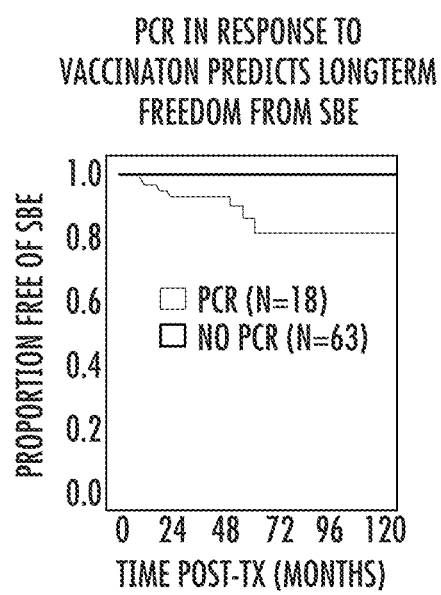

Example 2: Boosting anti-HER-2 CD4 Th1 Using DC1 Therapy in HER2$^{pos}$ Early Breast Cancer We have now conducted four clinical trials: two in patients with HER2$^{pos}$ DCIS and two in patients with HER2$^{pos}$ IBC. See: Lowenfeld L, et al. *Clin Cancer Res.* 2017;23:2961-71. All four studies have documented that we can increase the anti-HER2 CD4 Th1 response in peripheral blood with DC vaccine administration which does not really correlate with response to therapy but does demonstrate that administration of DC1 boosts anti-HER2 CD4 Th1. The DCIS patients received just four-six weekly vaccines either in distant groin lymph nodes or in the region of the DCIS in the breast, while the invasive patients received the initial six weekly intranodal followed by three month intranodal boosts ×3. Eighty five percent of the patients demonstrated an increase in anti-HER2 CD4 Th1. In the two DCIS studies where DC1 were administered in the neoadjuvant setting, about 30% of the ER$^{neg}$ patients demonstrated a pCR to DC1 vaccinations (FIG. 2A) and for the ERPOS HER2$^{pos}$ patients, adding anti-estrogen therapy with DC1 vaccination improved the pCR rate to similar level (FIG. 2A), from minimal background response indicating the efficacy of the combination approach. DC1 therapy was effective independent of whether administered in distant nodes or in the DCIS region in the breast. Interestingly those who achieved pCR demonstrated the highest levels of anti-HER2 CD4 Th1 in sentinel nodes (FIG. 2B). This indicates that achieving a significant anti-HER2 CD4 Th1 response in the local regional area of the tumor has the strongest clinical response and prompted us to study this further in preclinical models leading to our current effective therapy of DC1. Although there are low numbers of subjects achieving a pCR in DCIS from DC1 therapy it portends a very favorable reduction in any subsequent breast events ((SBE), FIG. 2C) compared to those achieving <pCR, something that would be critical to reduce recurrence and reduce mortality in high risk DCIS patients. We have studied the impact of DC1 therapy and Th1 cytokines on disseminated cancer cells (DCC) as that may be crucial to reduce mortality. For patients with IBC T1a/b lesions in their DCIS there was only about 8% incidence of finding no residual disease at surgery. It is clear that this therapy has shown promise but needed to be improved to be developed as satisfactory therapy for the group of patients with HER2 expressing DCIS and T1a/b IBC. Thus, we returned to preclinical models to build upon this opportunity.

Example 3: DC1 Vaccines in Combination with SEMA4D Blockade

Figure 3A:
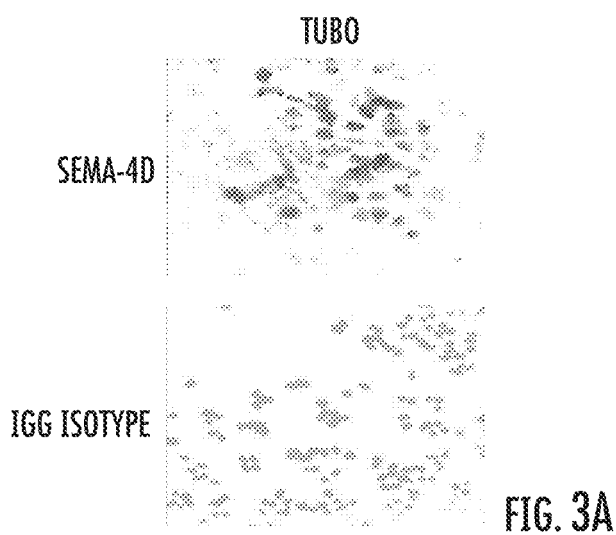
FIG. 3A-3G show Intratumoral DC1 in combination with anti-SEMA4D antibody induced tumor regression in HER2 positive TUBO model.

Semaphorin 4D (SEMA4D) is a member of family of cell surface molecules that are essential for tissue and organ development and are involved in immune regulation. Antibodies against SEMA4D have been shown to regulate lymphocyte infiltration into tumors (see, e.g., U.S. Pat. No. 9,243,068). In this Example, we combined an anti-SEMA4D monoclonal antibody (Mab 67, see, e.g., U.S. Pat. No. 8,496,938, with DC1 vaccinations in a HER2 murine TUBO tumor model as follows. The TUBO mouse mammary tumor cell line (Accession No. CVCL_2A33, Rovero, S., et al., *J. Immunol* 165:5133-5142 (2000)) was first shown to express SEMA4D by immunohistochemistry (FIG. 3A). For single tumor model (FIG. 3B1), Balb/C mice received 2.5e5 TUBO cells subcutaneously on right flank on day 0. When tumors were palpable on day 7, mice were randomized into four groups. Mice received monotherapy with either control antibody or anti-sema4D antibody intraperitoneally until end point or intratumoral HER2-DC1 weekly for six weeks. For combination therapy, mice received anti-sema4D antibody prior to receiving first intratumoral HER2-DC1 injection once a week for six weeks. For bilateral model, Balb/c mice (N=6) were injected at both flanks subcutaneously with $2.5 \times 10^5$ tumor cells/site on day 0. DC were generated, matured to DC1 as described previously (Cintolo J A, 2016, *Melanoma Res.* 2016 February; 26(1):1-11) and pulsed with neu peptides. BALB/c mice received DC vaccines intratumorally once a week for six weeks. In those animals with two tumor locations, that vaccine was administered in only one of the two tumors. Mab 67 was given intraperitoneally at the concentration of 10 mg/kg/body weight at weekly interval. Control mice received isotype control antibodies, DC treatment or Mab 67 alone. Tumors were measured every 2-3 days with a caliper until the endpoint. For comparison of in vitro measurements, a one-way ANOVA (followed by Tukey post hoc test) was performed. For comparison of in vivo measurements, the same test was performed using tumor measurement taken at each time point. A Mann-Whitney test was used to compare between two treatment groups. All statistical evaluations of data were performed using GraphPad Prism software. Statistical significance was achieved at p<0.05.

Figure 3B:
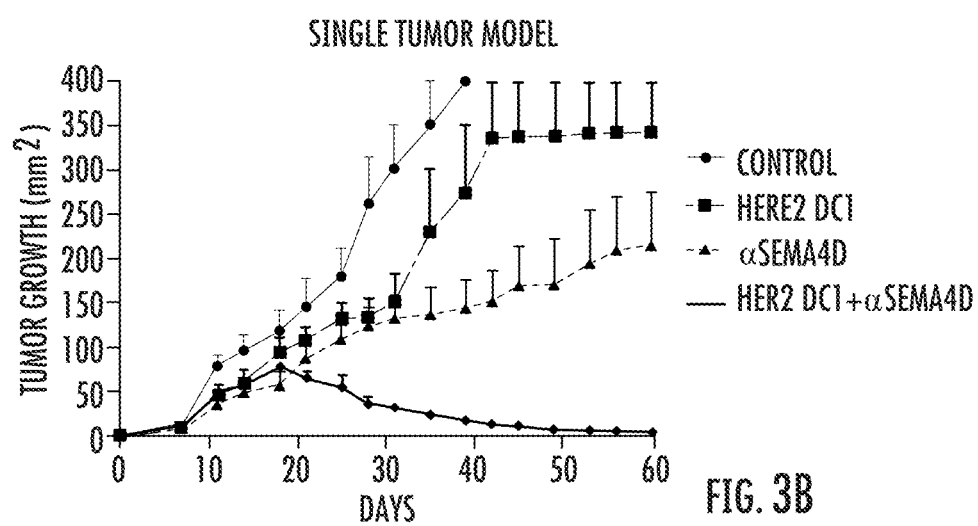
Figure 3C:
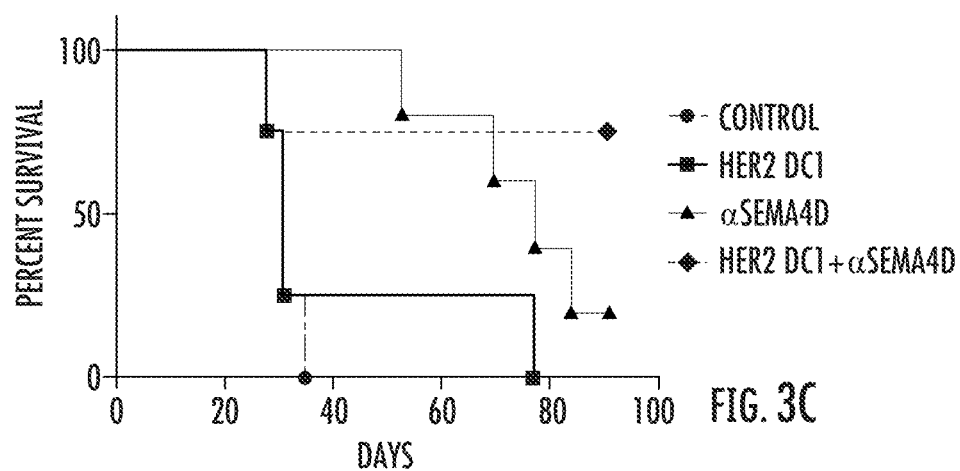
Figures 3D, 3E:
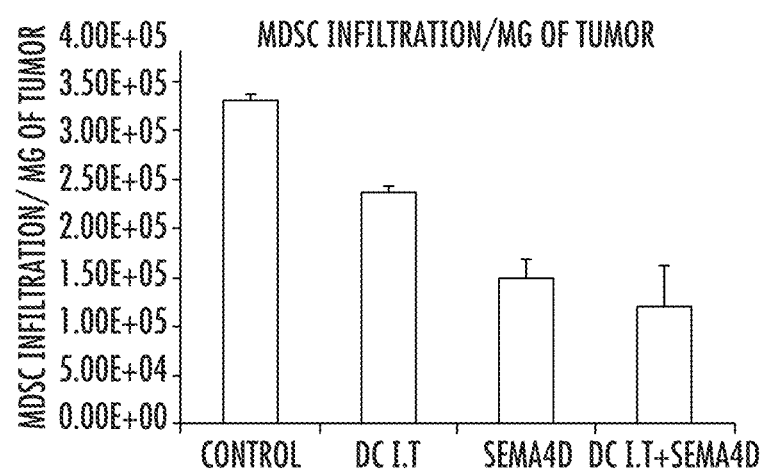
Figure 3F:
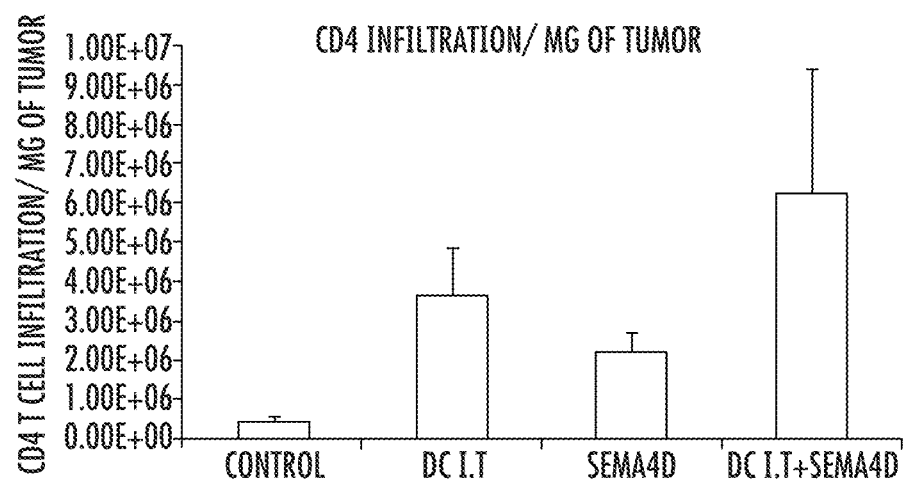
Figure 3G:
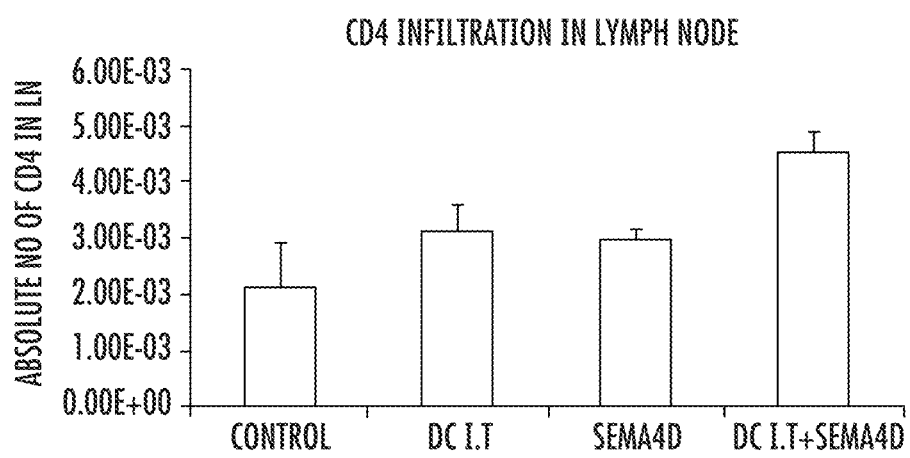

Systemic administration of the anti-SEMA4D antibody with intratumoral HER2 pulsed DC1 to mice bearing established TUBO tumors resulted in complete tumor regression of the vaccine-treated tumor compared to treatment with the anti-SEMA4D antibody or the DC1 alone (FIG. 3B1). This translated to increased survival (FIG. 3B2). An intratumoral injection of HER2 DC1 to a single tumor resulted in regression of non-injected contralateral tumors (FIG. 3C1 and 3C2). Further flow cytometric analyses demonstrated enrichment of anti-HER2 CD4 Th1 responses including reduced myeloid-derived suppressor cell tumor infiltration (FIG. 3E), increased CD4 T cell tumor infiltration (FIG. 3F), and increased CD4 T cell lymph node infiltration (FIG. 3G). The potential relevance to human tumors is highlighted by the fact that SEMA4D was expressed in about 60% of human HER2 DCIS or HER2 IBC as measured by immunohistochemistry (FIG. 3D).

Example 4: Administration of Intratumoral HER2 Pulsed DC1 and Systemic Anti-SEMA4D Antibody Resulted in Strong Anti-Tumor Th1 Responses Spleens were harvested from mice that were rendered cured of TUBO tumors by the combination systemic administration of anti-SEMA4D antibody with intratumoral HER2 pulsed DC1 therapy as described in Example 3, as well from control mice vaccinated intratumorally with the DC1 vaccine alone or in combination with anti-SEMA4D antibody, and CD4+ T cells were isolated from splenocytes were co-cultured with with HER2 pulsed DC1 for three-four days followed by expansion in the presence of IL-2 (10 U/ml) and IL-7 (20 ng/ml for three weeks. Cells expanded from spleens harvested from mice vaccinated with HER2 pulsed DC1 either alone or in combination with systemic anti-SEMA4D antibody treatment were compared (FIG. 4). The data indicate the CD4 T cells from mice given combination therapy displayed an in vitro expansion of about 7-fold compared to that of the control mice of about 3-fold (FIG. 4A). The CD4 T cells expanded from the spleens of mice given the combination therapy also displayed strong antigen specificity for HER2/neu-derived peptides p5, p435, and p1209 (see, e.g., Jalali et al., *Nanomedicine;* 8:692-701 (2012)) as compared to the CD4 T cells expanded from mice that received the DC1 vaccine alone (FIG. 4B). Moreover, the CD4 T cells expanded from the spleens of mice given the combination therapy displayed a strong production of IFN-γ indicating a strong TH1 response (FIG. 4C). These results show that CD4 T cells from HER2-DC1+aSEMA4D treated mice were superior in proliferation, function and specificity compared to T cells from HER2-DC1 alone vaccinated mice.

Figure 5A:
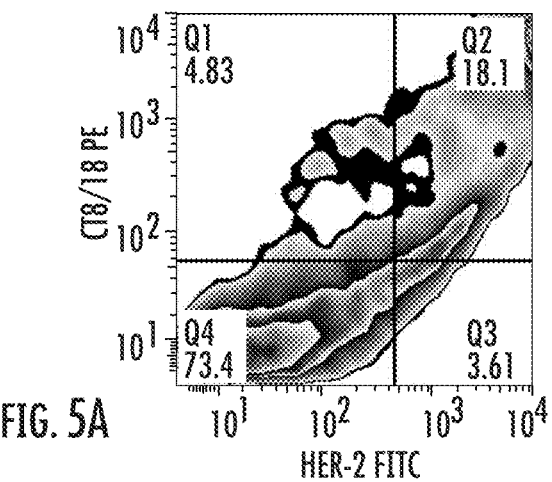
FIGS. 5A, 5B, and 5C show detection of DCC in neu Transgenic mice.
Figure 5B:
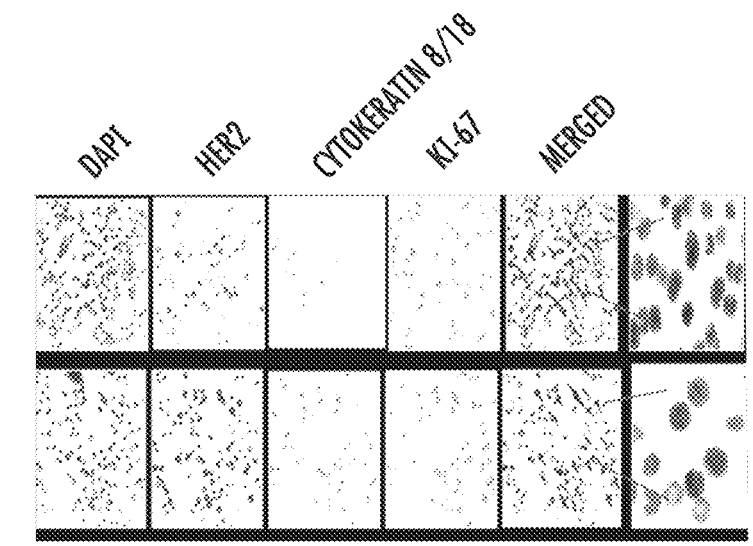
Figure 5C:
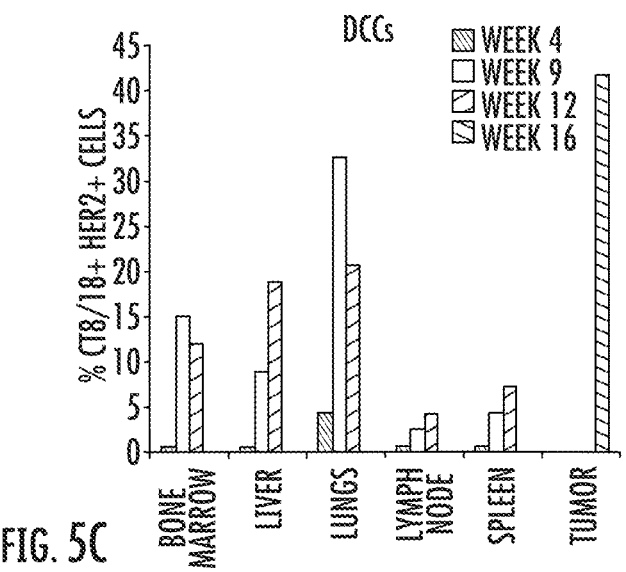
Figure 6A:
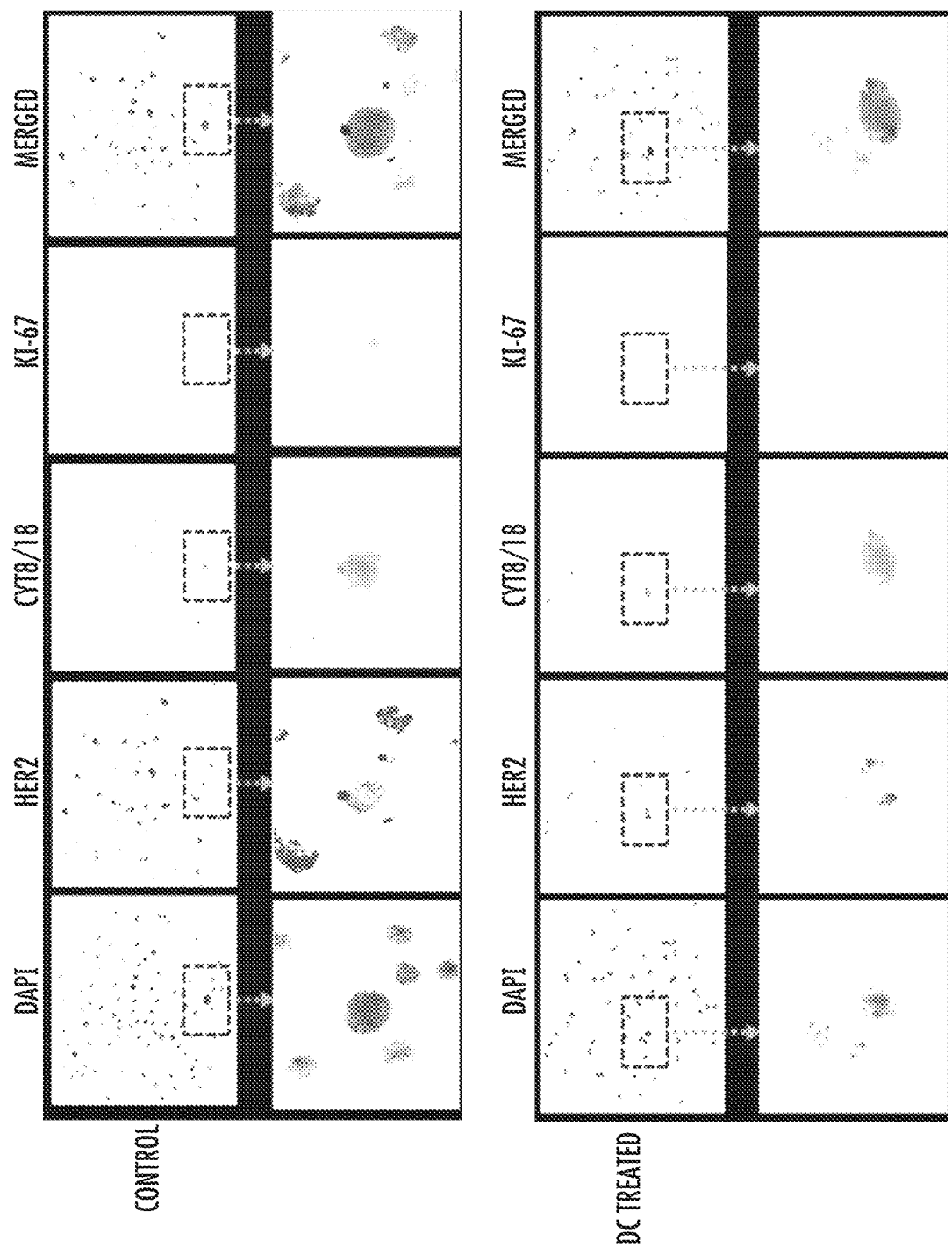

Example 5: DC1 Treatment of BALB/c Neu T Transgenic Mice Impacts Disseminated Cancer Cells in HER2 Expressing Mammary Carcinoma The DC1 vaccines were tested in HER2 patients with residual disease following neoadjuvant chemotherapy/trastuzumab, the DC1 administration was safe and resulted in increased anti-HER2 CD4 Th1 and there have been no recurrences in 17 patients with median follow-up of 40 months. Since many of these patients destined to recur would be harboring disseminated cancer cells (DCC), we wanted to study the effects of Th1 cytokines and as well as CD4 Th1 cells on DCC. For this we utilized the BALB/c Neu T transgenic mouse model. NeuT is a transgenic mouse model of breast cancer in which the mouse mammary tumor virus (MMTV) promoter drives neuT expression and mice develop spontaneous tumors in the mammary fat pads of female mice. When female BALB-neuT mice reach 21-28 d of age, the neuT protein is overexpressed in mammary glands and areas of atypical hyperplasia start to form, which progress to in situ carcinomas at about day 60 and to invasive cancers by day 120-150 Neoplastic change occurs, albeit asynchronously, in all mammary glands so that by about day 120, one or more tumors are palpable and by about day 230 all 10 mammary glands contain palpable tumors. We and others have demonstrated there are disseminated cancer cells that can be identified in several organs prior to the appearance of mammary carcinomas (FIG. 5A and 5B). These HER2+ cytokeratin positive cells can be detected in the bone marrow, lungs and liver from week 9 on and they compose 10-15% of the cells and are in a reasonably low proliferative state as measured by Ki67 (FIG. 5C). Vaccination of mice with HER2 pulsed DC1 after week 9 when DCC are present but prior to the development of mammary carcinoma resulted in a decrease in DCC as well as a decreased expression of Ki67 (FIG. 6A). DC1 Vaccines reduced the development of mammary carcinoma at week 16 (FIG. 6B). There was also a diminished number of DCC (FIG. 6C) and increase in markers of tumor senescence in DCC from Neu T mice treated with DC1. Shown in FIG. 6D is β-galactosidase expression a common marker of senescence. This latter data indicates that, besides the impact of therapy on primary or metastatic disease, with intratumoral therapy, DC1 can through induction of anti-HER2 CD4 T cells drive senescence and protect against tumor development and may have an impact on BC mortality.

Example 6: Immune Cell Infiltration After DC1 or SEMA4D Treatment

Figure 7A:
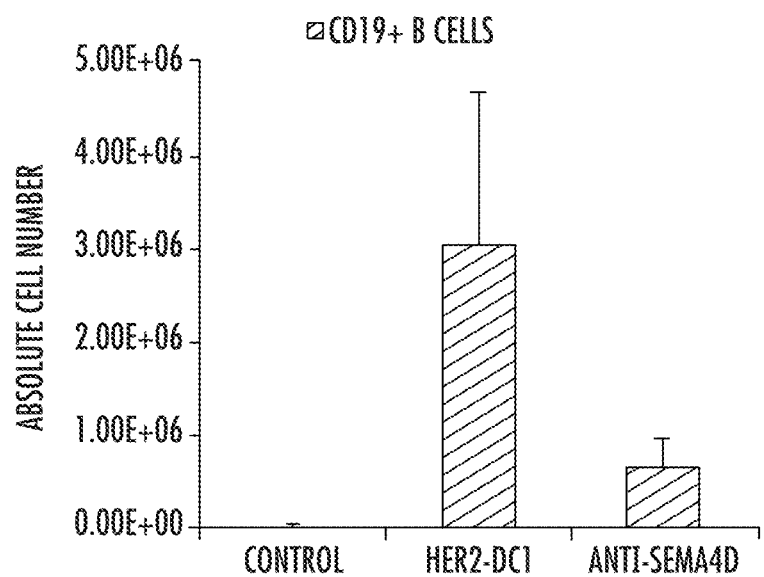
FIGS. 7A and 7B show that HER2 peptide pulsed DC1 vaccine and anti-SEMA4D treatment induced infiltration of B cells in the mammary glands and CD4+ T cell infiltration in bone marrow of NeuT mice.
Figure 7B:
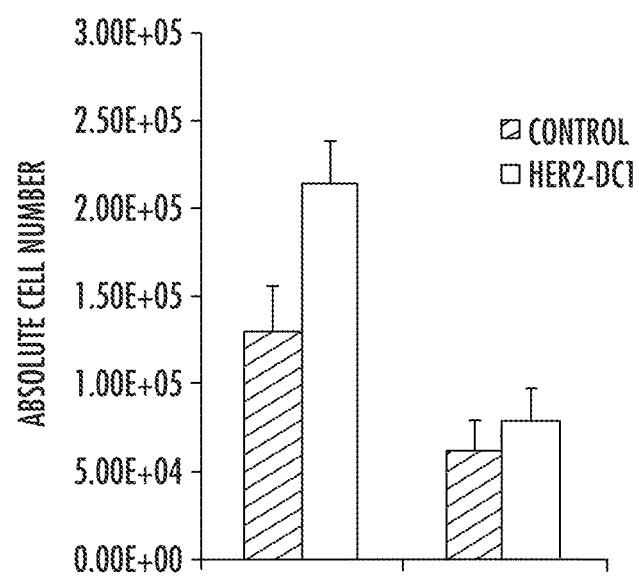

BALB-neu transgenic (Neu T) mice were treated at 8 weeks of age with subcutaneous injections of $1\times10^6$ rat neu peptide-pulsed DC1 twice a week or with anti-SEMA4D antibody administered weekly at a concentration of 10 mg/kg/body weight. On week 16, the mice were sacrificed, and mammary glands were collected. The single cell suspension of mammary glands was prepared and stained for CD19 positive B cells then analyzed by flow cytometry. An increased level of CD19+ B cells was observed in DC1 vaccinated mice and in anti-SEMA4D antibody-treated mice compared to untreated control, indicating B cell infiltration into the mammary glands (FIG. 7A). The accumulation of B cells in the tumor region indicates that antitumor antibodies play a role in causing the effects seen in DC1 therapy with SEMA4D. In addition, the bone marrow cells derived from the control and DC1 vaccinated NeuT mice were stained for CD4 and CD8 T cell markers and analyzed by flow cytometry. Increased numbers of CD4T cells and CD8 T cells were observed in the bone marrow of DC1 vaccinated NeuT mice compared to untreated control mice (FIG. 7B).

Figure 8A:
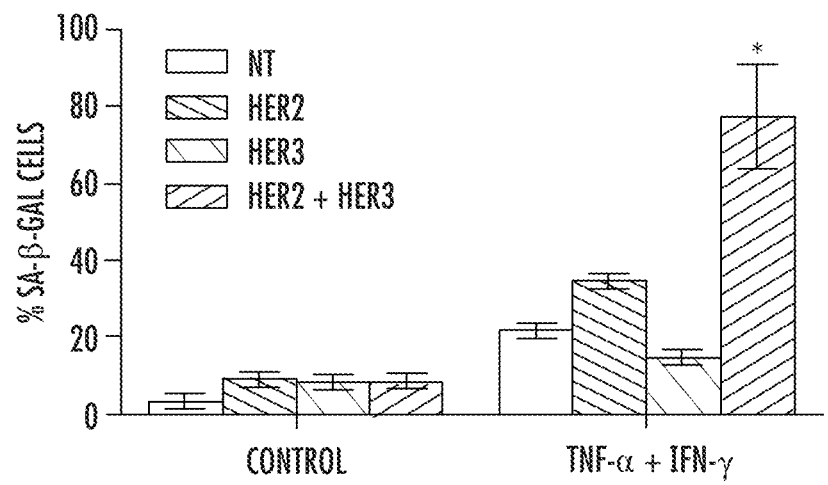
FIGS. 8A, 8B, 8C, 8D, and 8E show Dual Blockade of HER2 and HER3 in combination with Th1 cytokine mediates tumor senescence and apoptosis in SK-BR-3 breast cancer cells.
Figure 8B:
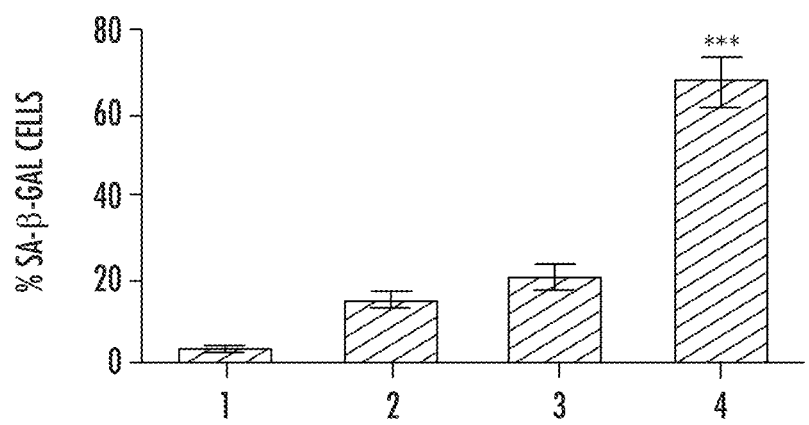
Figure 8C:
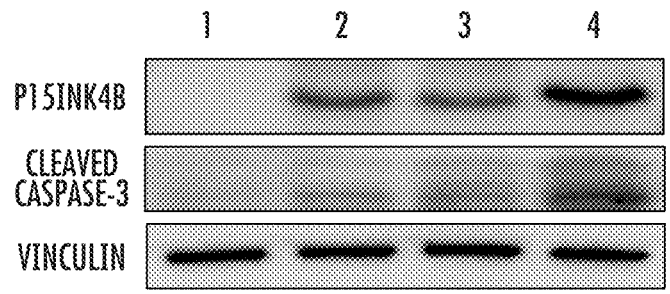
Figure 8D:
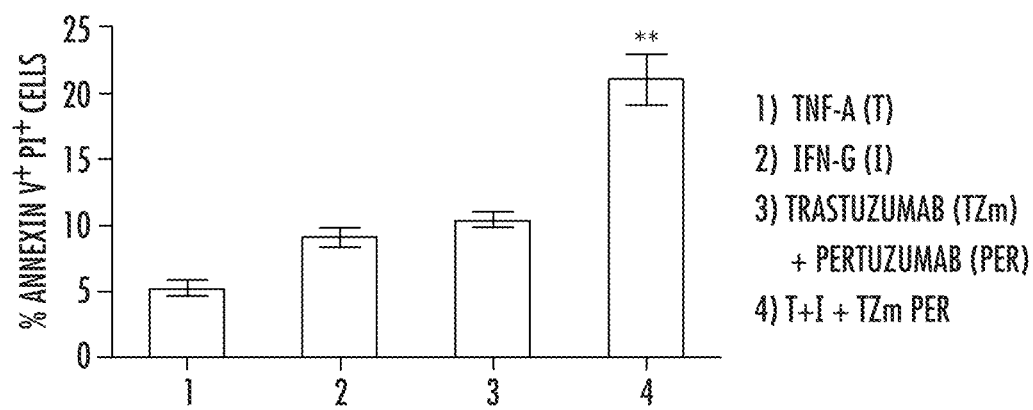
Figure 8E:
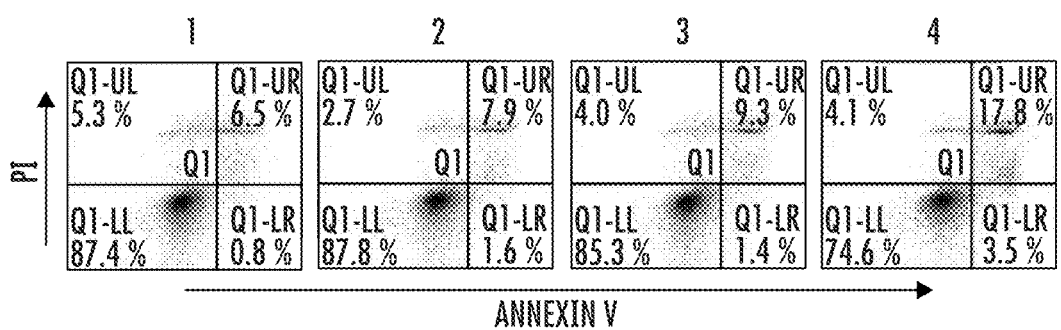

Example 7: IFN-γ and TNF-α from CD4 Th1 Cause Induction of Tumor Senescence in HER2 Expressing Breast Cancer Since CD4 and B cells (MHC class II APC) accumulate around the DCIS ducts, we investigated the impact of Th1 cytokines on HER2 BC cells. IFN-γ and TNF-α cause the induction of both apoptosis and tumor senescence in HER2 expressing BC cells. The therapeutic benefit of blocking HER2/HERS signaling in breast cancer has been demonstrated in both in vitro studies and clinically. We explored the senescent and apoptotic effects of Th1 cytokines in high and intermediate HER2-expressing cell lines blocked with HER2 and HER3 siRNA (FIG. 2). Although the combined treatment of TNF-α and IFN-γ in HER3-knocked down SK-BR-3 cells did not significantly enhance the number of senescent cells, higher SA-β-gal staining was observed in cells treated with dual HER2/HER3-knocked down combined with Th1 cytokines (FIG. 8A). Trastuzumab, a humanized recombinant monoclonal antibody directed against the extracellular subdomain IV of HER2, inhibits ligand-independent dimerization, blocks downstream proliferation signaling pathways, and induces antibody-dependent cellular cytotoxicity (ADCC) and Pertuzumab, another humanized recombinant monoclonal antibody targeting the extracellular subdomain II of HER2, prevents ligand-dependent heterodimerization with other members of the HER family, which also inhibits proliferation signaling pathways and induces ADCC. Together both antibodies act in a complementary fashion. We applied our paradigm of Th1 cytokine-induced senescence and apoptosis to a combination model, using TNF-α and IFN-γ treatment together with trastuzumab and pertuzumab. In HER2high SK-BR-3 cells, we found that senescence increased synergistically in cells treated with the combination of cytokine and antibodies compared to untreated cells, cells treated with cytokines alone, or cells treated with antibodies alone, as measured by SA-β-gal staining (FIG. 8B, p<0.001) and p15$^{INK4b}$ expression(Cyclin-dependent kinase 4 inhibitor B, also known as p15$^{INK4b}$) (FIG. 8C). Notably, the combined treatment not only induced a relatively higher percentage of blue senescent cells, but there were also significantly fewer cells overall. Increased apoptosis in an additive fashion was demonstrated by increased active caspase-3 expression (FIG. 8C) and increased annexin V and propidium iodide positive cells (FIG. 8D & E). We explored the potential for TNF-α and IFN-γ to induce senescence and apoptosis in trastuzumab and pertuzumab resistant cell lines. HCC-1419 and JIMT-1 cells were treated with trastuzumab and pertuzumab did not induce senescence or apoptosis (FIG. 9). However, the dual treatment with cytokines and targeted therapies induced significantly greater senescence as evidenced by SA-β-gal assay (FIG. 9A) and increased expression of p15$^{INK4b}$ in HCC-1419 cells (FIG. 9B) and JIMT-1 cells (FIG. 9C). Th1 cytokines combined with HER2/HER3 blockade can cause tumor senescence and apoptosis even in cell lines resistant to trastuzumab and pertuzumab.

Figure 10A:
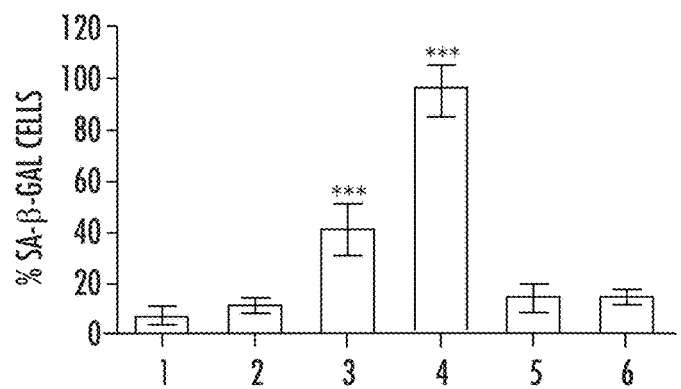
FIGS. 10A and 10B show HER2-specific CD4+ Th1-mediated senescence and apoptosis of HER2-ovexpressing human breast cancer cells.
Figure 10B:
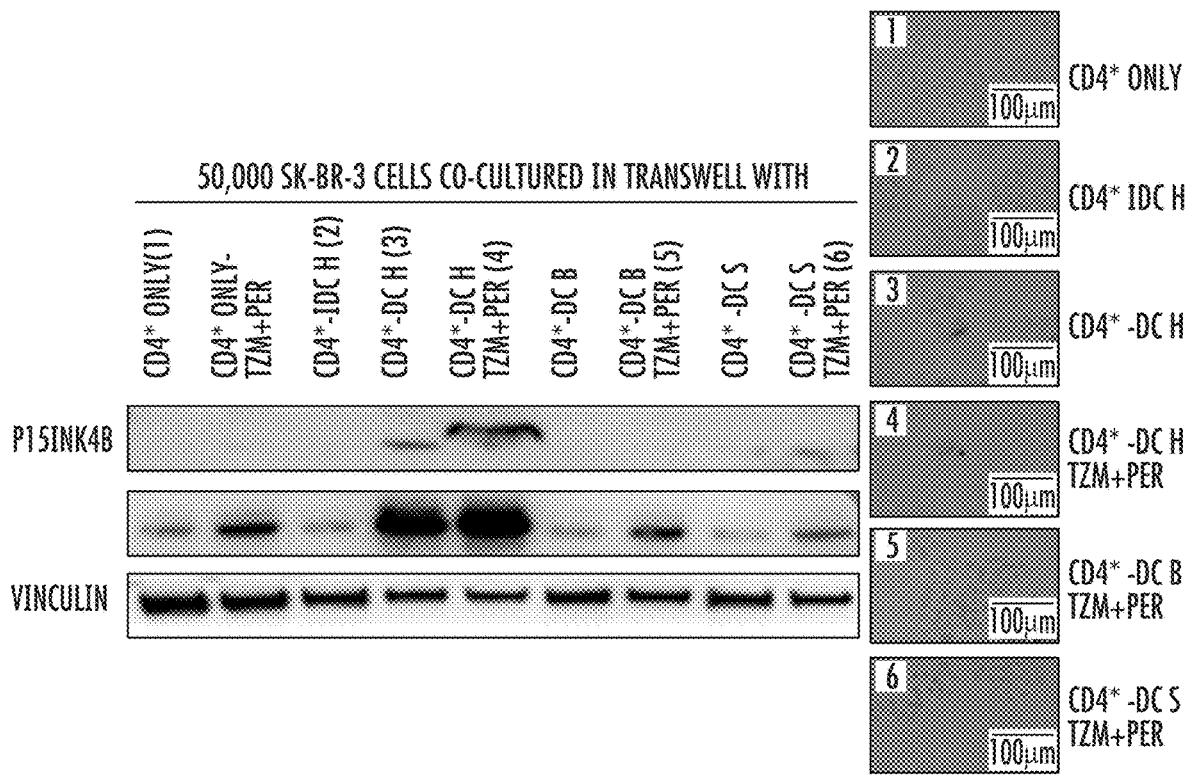

We next tested whether anti-HER2 CD4 Th1 cells could impact HER2$^{pos}$ BC cells separated by transwell membrane. SK-BR-3 breast cancer cells co-cultured with CD4+ T-cells from breast cancer patients primed with Class II HER2 peptides resulted in senescence and apoptosis of SK-BR-3 cells, evidenced by increased SA-β-gal staining (FIG. 10A) and p15$^{INK4b}$ and cleaved caspase-3 expression (FIG. 10B, CD4+- DC H, 3). CD4+ T-cells primed either with immature dendritic cells (CD4+- IDC H (2)) or mature DCs plus irrelevant Class II peptides (BRAF: CD4+- DC B (5); or survivin: CD4+- DC S (6)) were not able to induce senescence or apoptosis of SK-BR-3 cells. Similar to the previously demonstrated synergistic effect, senescence and apoptosis were significantly augmented when trastuzumab and pertuzumab (4) were added to the culture, evidenced by increased SA-β-gal staining (FIG. 10A, p<0.001) and p15$^{INK4b}$ and cleaved caspase-3 expression (FIG. 10B, CD4+- DC H TP, 4). These results indicate that the anti-HER2 CD4 Th1 cells do not need to interact directly with the tumor cells but rather antigen presenting cells (APC) in the TME, and the Th1 cytokines can synergize with HER2 targeted therapy. This may form the basis of having DC1 pulsed and bound in the tumor environment to drive anti-HER2 CD4 Th1 responses and the possibility that antibodies like HP can synergize with Th1 cytokines to eliminate tumor cells.

Example 8: Clinical Activity of Th1 Cytokines (IFN-γ) in HER2 Breast Cancer

We have built on preclinical findings by developing a Phase I/II study investigating whether IFN-γ can be administered safely and have effects in clinical response. A Phase I study demonstrated IFN-γ administered subcutaneously three times a week with THP in patients with first line metastatic BC was safe and resulted in disease stabilization of partial responses (FIG. 11). This has now progressed to a Phase II study being administered in a neoadjuvant setting to those with >T2 ER+HER2+ IBC. 15 patients are now enrolled and two of the first four patients have had a pCR. We are encouraged by this as this subtype of patients treated with PTCH, a significantly more toxic regimen, demonstrate about 27% pCR rate. As shown herein, this regimen is successful in at least maintaining the established pCR rate and thus, the regimen can replace the more toxic regimens with simpler potentially more effective regimen using a combination of immunotherapy with Th1 cytokines and standard therapy. We are determining whether DC1 vaccines can drive a similar response in neoadjuvant HER2 patients to drive pCR in combination with PTCH. These data point to the clinical benefits of Th1-cytokines like IFN-γ to impact HER2 tumors and are poised to become components of the true non-chemotherapy regimens in HER2 BC.

Figure 12A:
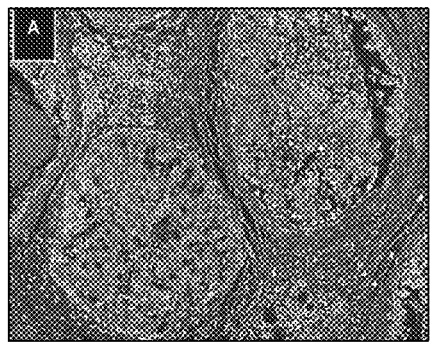
FIGS. 12A, 12B, 12C, and 12D show immunohistochemical staining of lymphocyte infiltration before and after DC1 vaccine in DCIS.
Figure 12B:
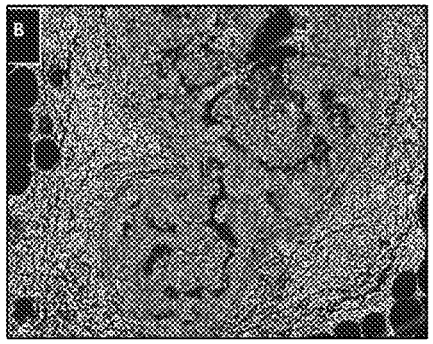
Figure 12C:
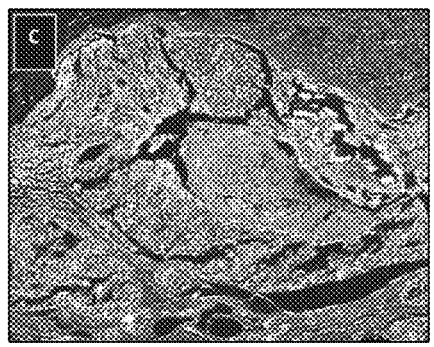
Figure 12D:
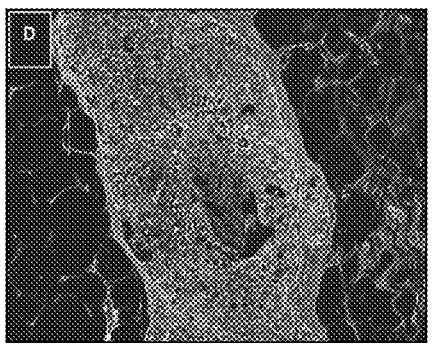
Figure 13:
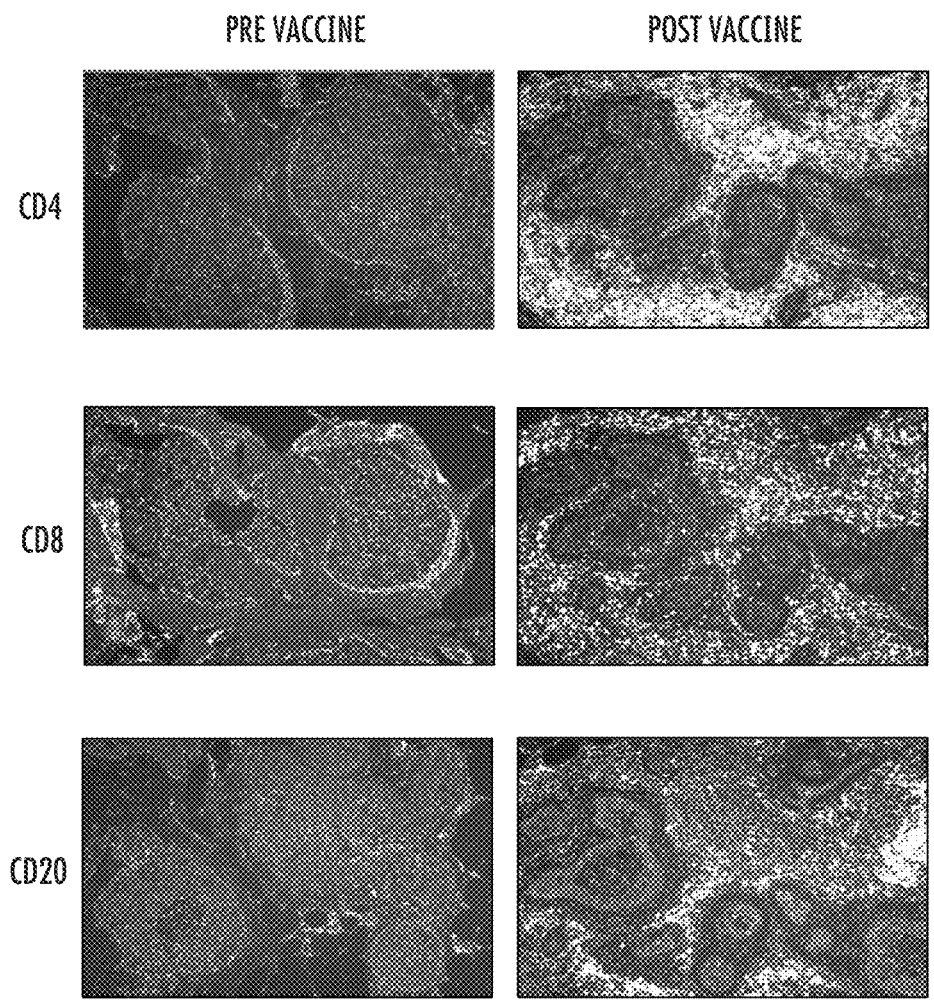
FIG. 13 shows accumulation of lymphocytes pre and post DC1 vaccination in DCIS. CD4, CD8 and CD20 infiltration is shown.
Figure 14:
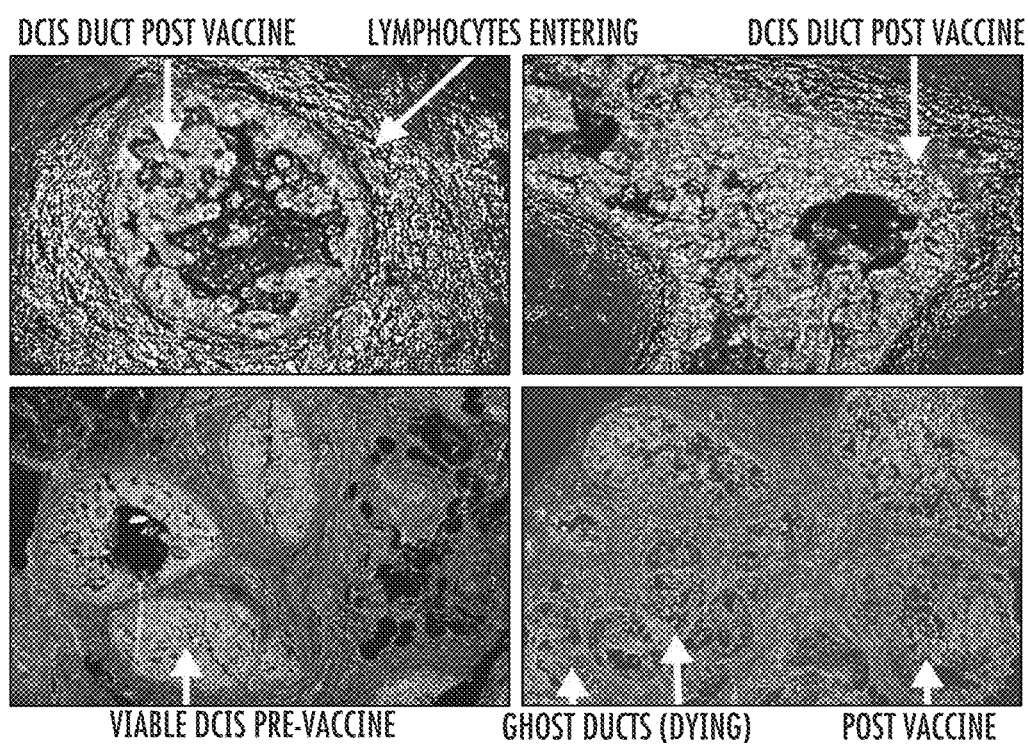
FIG. 14 shows Lymphocytes infiltration in DCIS ducts after DC1 vaccination.

Example 9: Accumulation of B and T Cells Occurs in Patients Responding to HER2-pulsed DC1 Vaccines Although patients with pCR demonstrate no residual DCIS ducts in the breast, many of those with residual disease affords the opportunity to assess the response in the breast of those with residual disease. The response in the breast is often heterogeneous with areas of dense lymphocytic infiltrate (FIG. 12A & B) and areas with little or no response (FIG. 12C & D). The accumulation of lymphocytes represents a large fraction of CD4 T cells as well as CD20+ B cells and some CD8 T cells (FIG. 13). These structures mimic ectopic lymphoid structures which are associated with favorable responses. In patients with significant accumulation of these lymphoid structures in and around DCIS ducts we often see dying or dead ducts, indicating the immune response is causing death and elimination of DCIS (FIG. 14).

Effect of Anti-SEMA4D Antibody on the TME and Tumor Vasculature

Figure 15A:
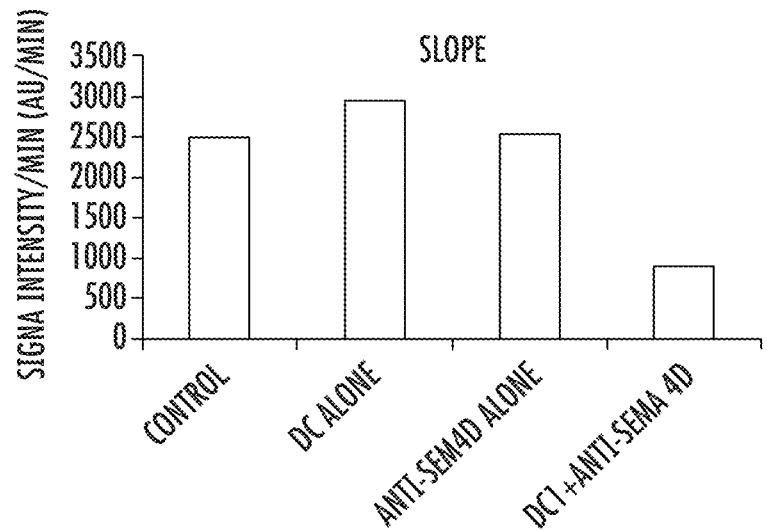
FIGS. 15A and 15B show combination therapy with intratumoral DC1 and anti-SEMA4D improves tumor vascularity.
Figure 15B:
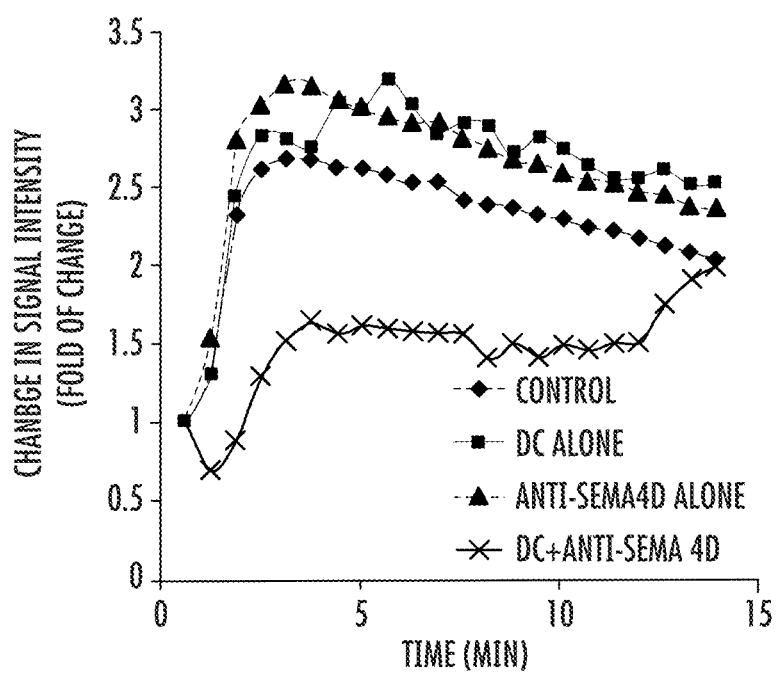

SEMA4D has been described as a promoter of angiogenesis of tumors and, therefore, has been associated with tumor progression (see, e.g., Zhou, et al. Methods Mol. Biol 1493:429-441 (2017)). To study how SEMA4D modifies TME, specifically tumor vascularity, we observed tumor vascularity in mice injected with TUBO cells as described in Example 3 by in-vivo MRI. Dynamic Contrast Enhancement (DCE)—MRI were used to examine different properties of tumor vascularity: Using Area under curve (AUC), slope, time to maximum, we determined the status of tumor vascularity. We injected 0.2 mmol/kg of Gadavist through the tail vein to investigate how single treatments with DC1 alone or anti-SEMA4D alone or both agents in combination affect the tumor vascularity and regression of tumor. We observed smaller slope, less accumulation of the contrast agent, and less vessel leakage (FIG. 15A&B) in mice that received combination therapy compared to untreated or monotherapy. This data indicates that combination therapy with intratumoral DC1 with systemic administration of an anti-SEMA4D antibody improves tumor vascularity indicated by smaller slope and less accumulation of the contrast agent and less vessel leakage which may play a role in the inducing complete tumor regression in both single and bilateral TUBO model.

Example 10: Effect of Anti-SEMA4D on Tumor pH

Figure 16:
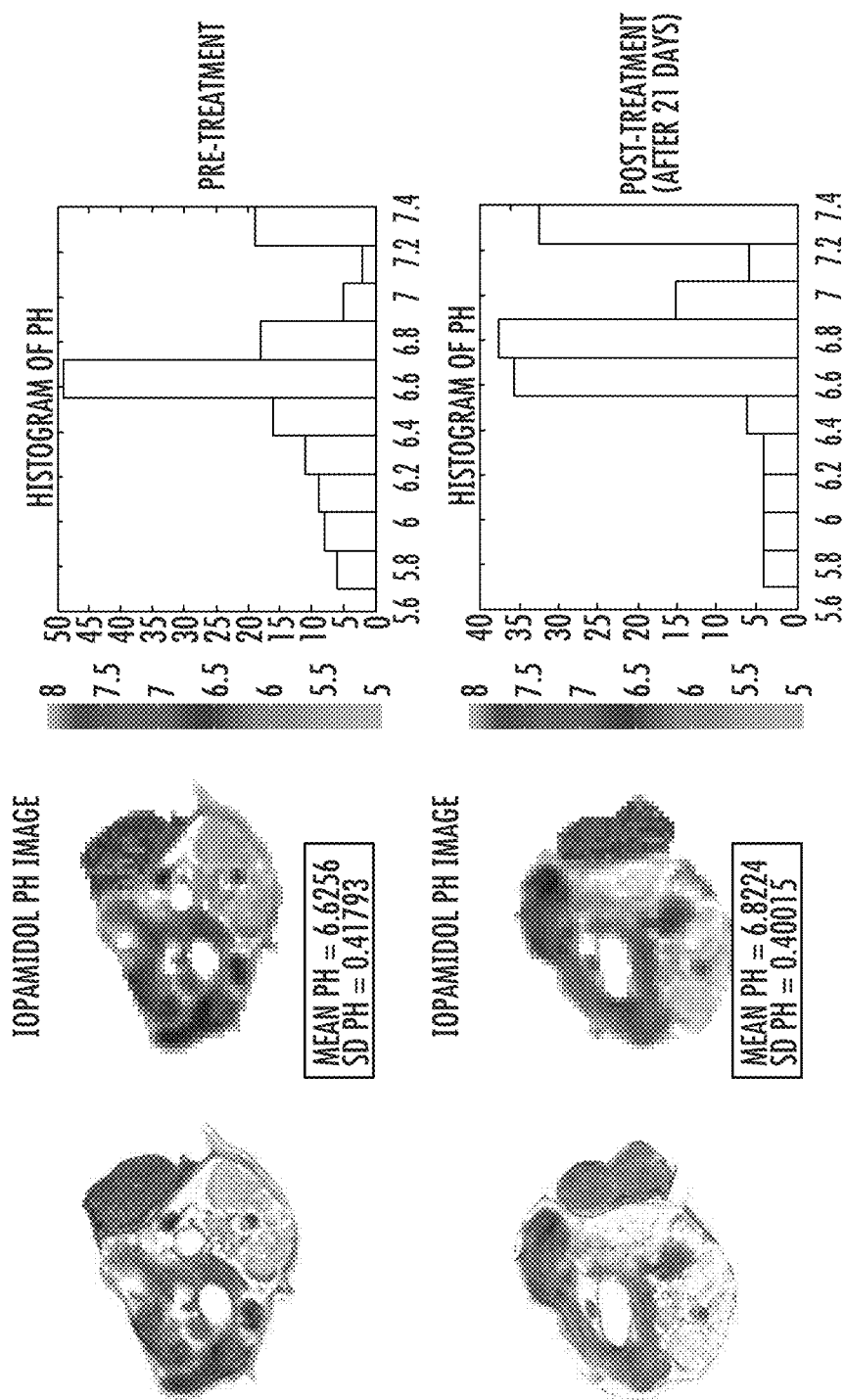
FIG. 16 shows CEST MRI (tumor pH) map of a TUBO tumor treated with anti-SEMA4D. From right to left: T2-weighted image representing the ROI, pH map the insertion shows the pH mean value and its Standard Deviation), and histogram representing pH values of all pixels calculated.

Effect of anti-SEMA4D on tumor pH:. Tumors have been shown to be acidic and tumor acidosis has been correlated with poor prognosis and greatly relies on vascularity to reduce their acidity, we examined tumor pH by means of Chemical Exchange Saturation Transfer (CERST)-MRI experiments. As shown in FIG. 16, we observed that treatment with SEMA4D alone had an effect on shifting tumor pH from acidic to alkaline over time.

The murine monoclonal antibody Mab 67, described above, is disclosed, e.g., in U.S. Pat. No. 8,496,938.

The amino acid sequences of the MAb 67 VH and VL genes are shown below with the CDR1, CDR2 and CDR3 regions underlined.

```
MAb 67 VH:
                                       (SEQ ID NO: 1)
QVQLQQSGPELVKPGASVKISCKASGYSFSDYYMHWVKQSPENSLEWIGQ
INPTTGGASYNQKFKGKATLTVDKSSSTAYMQLKSLTSEESAVYYCTRYY
YGRHFDVWGQGTTVTVSS

MAb 67 VL:
                                       (SEQ ID NO: 2)
DIVMTQSPASLAVSLGQRATISCKASQSVDYDGDSYMNWYQQKPGQPPKL
LIYAASNLESGIPARFSGSGSGTDFTLNIHPVEEEDAATYYCQQSNEDPY
TFGGGTKLEIK
```

1. Mab VX15/2503 (pepinemab) is a humanized version of MAb 67, and is also disclosed in U.S. Pat. No. 8,496,938. The amino acid sequences of VX15/2503 are reproduced below.

```
Sequence of VX15/2503 VH:
                                       (SEQ ID NO: 3)
QVQLVQSGAEVKKPGSSVKVSCKASGYSFSDYYMHWVRQAPGQGLEWMGQ
INPTTGGASYNQKFKGKATITVDKSTSTAYMELSSLRSEDTAVYYCARYY
YGRHFDVWGQGTTVTVSS Sequence of VX15/2503 VL:
                                       (SEQ ID NO: 4)
DIVMTQSPDSLAVSLGERATINCKASQSVDYDGDSYMNWYQQKPGQPPKL
LIYAASNLESGVPDRFSGSGSGTDFTLTISSLQAEDVAVYYCQQSNEDPY
TFGQGTKLEIK
```

Example 11: Depletion of CD4+ T Cells Abrogates Anti-SEMA4D Activity, Both Alone and in Combination with DC-1 Treatment As a whole, CD4+ T cells play a major role in instigating and shaping adaptive immune responses. To study whether CD4+T cells are necessary for a clinical response to combination HER2 DC1 vaccine/anti-SEMA4D treatment, CD4 depleted tumor-bearing mice were generated and the immune response to treatment was compared to that of non-CD4 depleted ("normal") tumor bearing mice.

Balb/C mice received 2.5e5 TUBO cells subcutaneously on the right flank on day 0. When tumors were palpable on day 7, the mice were randomized into four groups. Mice received monotherapy with either an IgG isotype control antibody or anti-SEMA4D antibody/MAb67 (10 mg/kg/body weight) intraperitoneally until end point or 1e6/100 µl intratumoral HER2-DC1 weekly for six weeks. For combination therapy, mice received anti-sema4D antibody prior to receiving a first intratumoral HER2-DC1 injection once a week for six weeks.

CD4 depleted Balb/C mice were generated by administering 300 µg of anti-CD4 depleting antibody (Clone GK1.4) intraperitoneally, starting three days before TUBO tumor implantation, and treatment with the anti-CD4 antibody continued with two injections per week until end point. (See Evans, E. E., et al. (2015). Cancer Immunol Res 3(6): 689-70) The CD4-depleted mice were treated with monotherapy, anti-SEMA4D antibody/MAb67, or combination therapy as described above for tumor-bearing non-CD4 depleted mice.

Figure 17A:
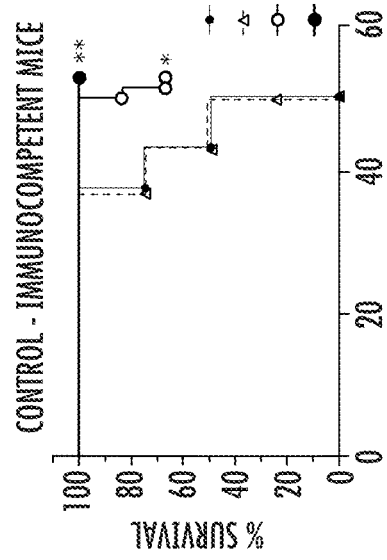
FIGS. 17A-F show that CD4+ T cells are required for anti-SEMA4D activity.
Figure 17B:
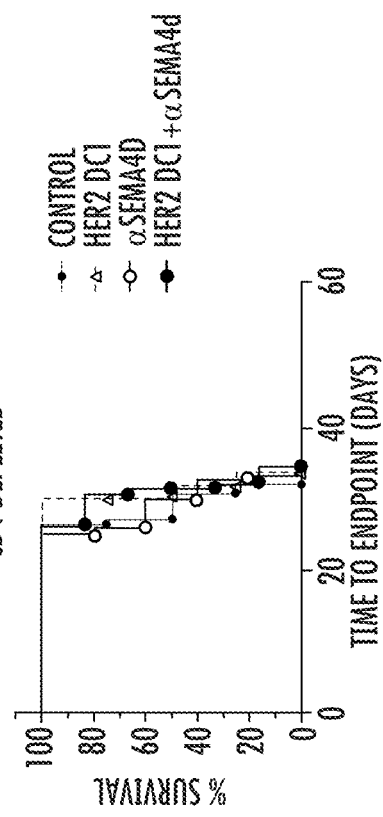
Figure 17C:
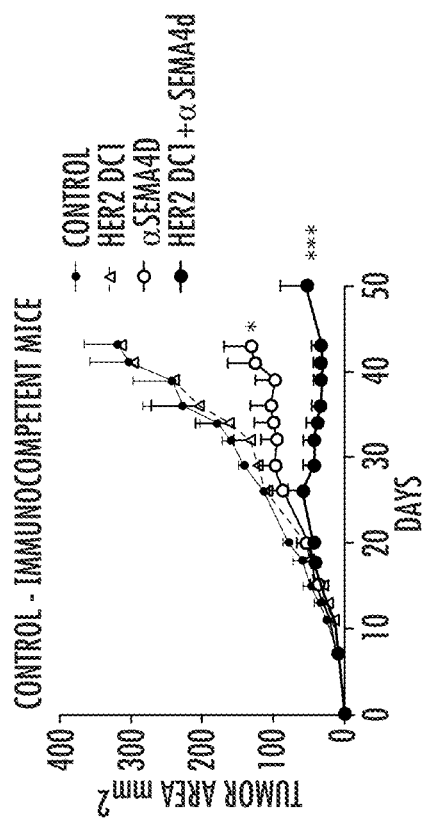
Figure 17D:
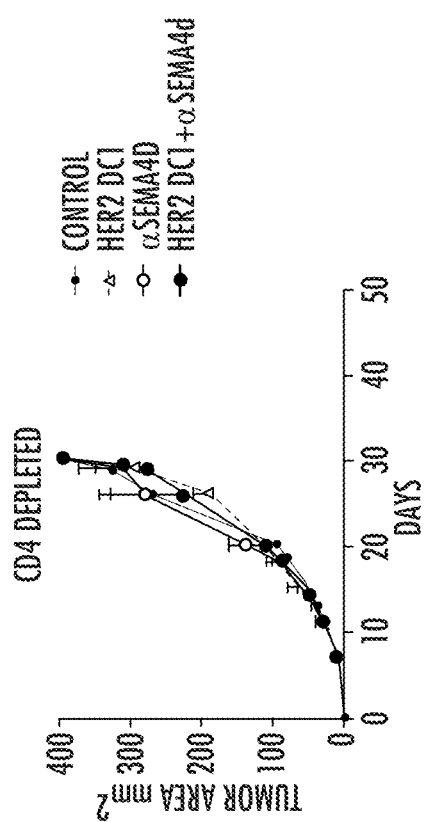
Figure 17E:
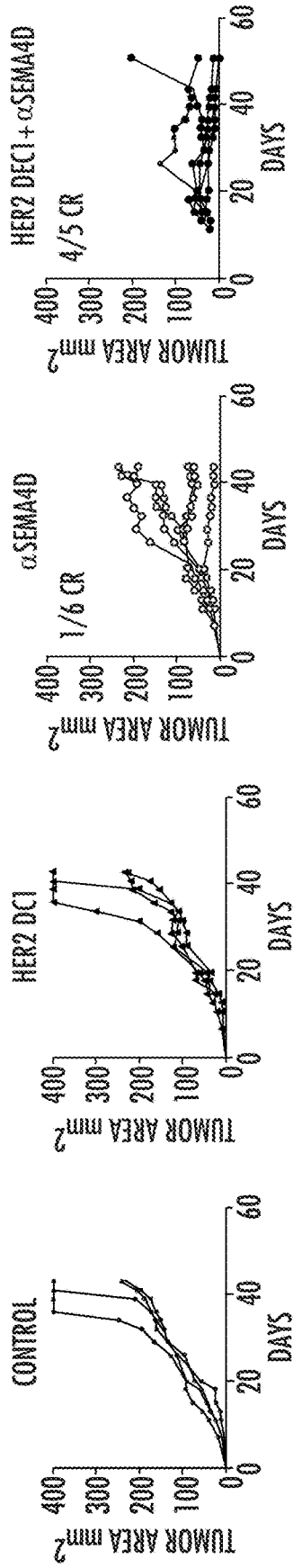
Figure 17F:
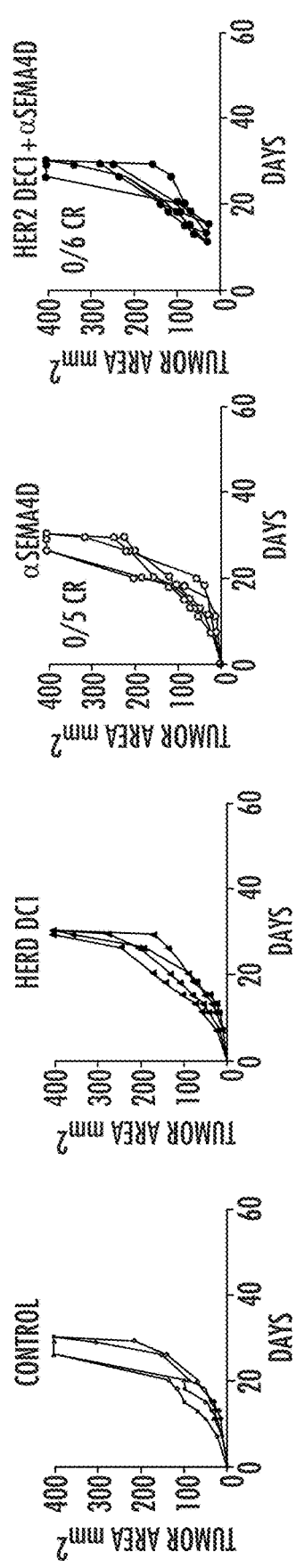

Mean tumor volume and survival for each group are shown in FIG. 17A-D-17A and B (Control, no CD4 depletion; tumor volume and survival, respectively), and 17C and D (CD4 depletion). FIGS. 17E (control, no CD4 depletion) and 17F (CD4 depletion) show tumor growth curves for each mouse. Complete tumor regression was observed following treatment with anti-SEMA4D and activity was further enhanced with the combination therapy. All of the combination-treated mice in the non-depleted group survived for the sixty-day testing period (FIG. 17B), and 4/5 of these mice showed complete tumor regression. (FIG. 17E). However, depletion of CD4+ T cells completely abrogated activity of anti-SEMA4D treatment, both alone and in combination with the DC-1 vaccine (FIG. 17D). These data indicate that CD4+ T cells are required for a clinically effective response to anti-SEMA4D therapies.

Example 12. Role of Fc Gamma Receptors (FcγR) on Clinical Effect of Combination Therapy The FcγR mediated functions most commonly associated with therapeutic antibodies are those that mediate target cell elimination—antibody-dependent cellular cytotoxicity (ADCC), which is a mechanism of cell-mediated immune defense whereby an effector cell of the immune system actively lyses a target cell, whose membrane-surface antigens have been bound by specific antibodies. These functions are triggered when antibody binding to antigen on the surface of a target cell generates sufficient avidity to trigger signaling through FcγRs on effector cells such as NK cells and macrophages, which then eliminate target cells through direct killing or phagocytosis. Preclinical models show that these forms of FcγR-mediated cytotoxicity are a significant component of the mechanism of action for certain tumor targeted antibodies. (Clynes R A et al., *Inhibitory Fc receptors modulate in vivo cytoxicity against tumor targets*. Nat Med. 2000, 6: 443-446).

To study the role of FcγR in the clinical response to the combination therapy, FcγR knock-out mice were generated. Briefly, the model was created by targeted disruption of the Fcer1g gene via introduction of a new stop codon in E14 ES cells and injecting the targeted cells into C57BL/6 blastocysts. Heterozygotes on a C57BL/6 background were intercrossed to generate homozygous targeted mutation mice. The mice were then backcrossed twelve generations (N12) to a BALB/cByJ inbred background. (Takai T, Li M, Sylvestre D, Clynes R, Ravetch J. (1994) *FcRγ Chain Deletion results in Pleiotrophic Effector Cell Defects.*).

Figure 18A:
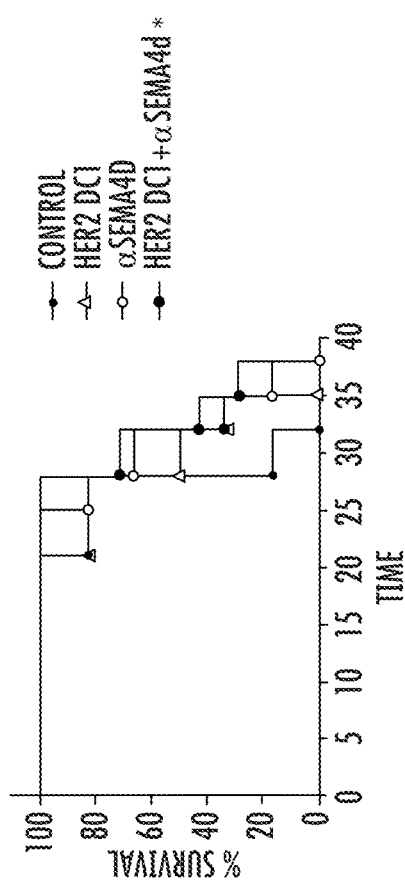
FIGS. 18A-C show that Fc Receptor gamma (FcRγ) is required for complete tumor regression following treatment with combination therapy.
Figure 18B:
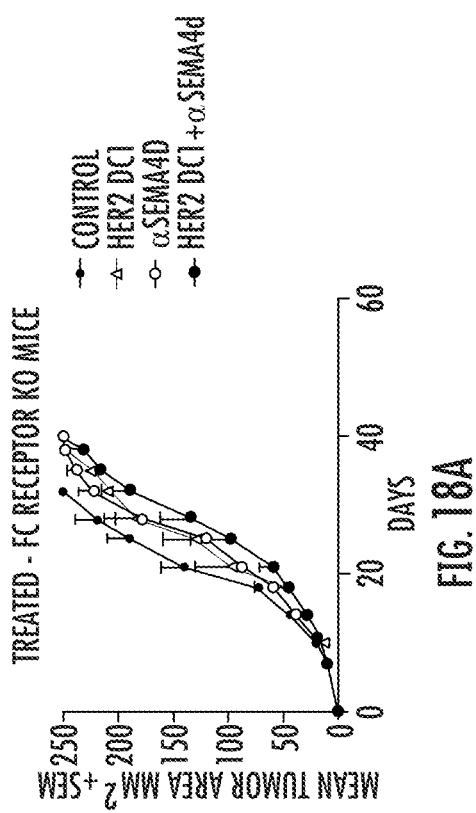
Figure 18C:
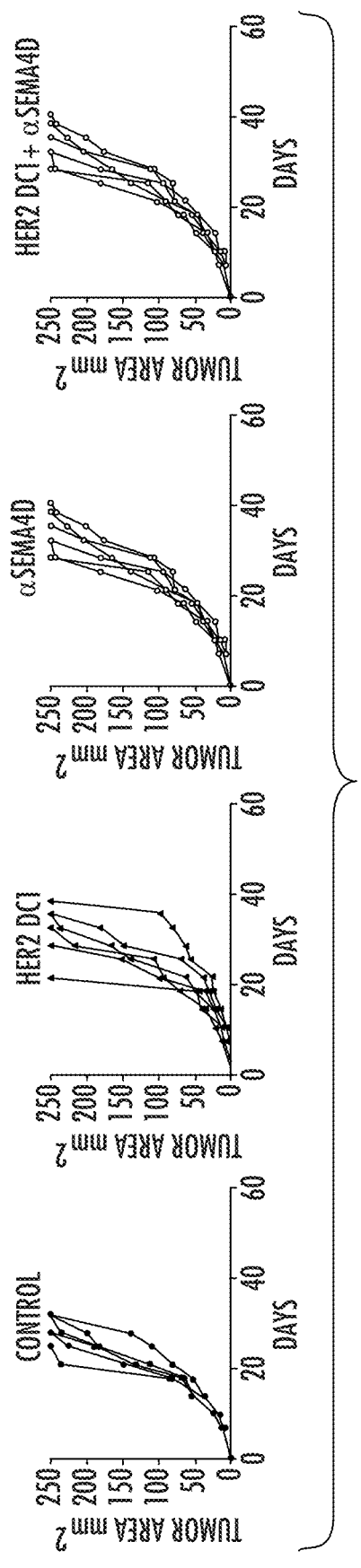

BALB/C-Fcer1g KO mice (C.129P2(B6)-Fcer1g$^{tm1Rav}$ N12) were injected at both flanks subcutaneously with 2.5×10$^5$ tumor cells/site on day 0. DC were generated, matured to DC1 and pulsed with MHC class II neu peptides. Mice received 1e6/100 µl DC1 vaccine intratumorally once a week for six weeks. In those animals with two tumor locations, the vaccine was administered in only one of the two tumors. Anti-SEMA4D Mab 67 was given intraperitoneally at a concentration of 10 mg/kg/body weight at weekly intervals. Control mice received isotype control antibodies, DC treatment or Mab 67 alone. Tumors were measured every 2-3 days with a caliper until the endpoint. Mean tumor volume of treated tumors and survival for each group are shown in FIG. 18A and 18B, respectively. Tumor growth curves for each mouse are shown in FIG. 18C. (CR=complete tumor regression; tumor volume <50 mm$^2$).

The data show that in mice lacking Fc Receptor gamma expression, the combination therapy significantly delayed tumor growth compared to no treatment or single agent treatment (FIG. 18A and B). However, complete tumor regression was not achieved (FIG. 18B), in contrast to control mice treated with combination therapy (FIG. 17E), which indicates that Fc Receptor gamma is essential for complete anti-tumor efficacy of the combination therapy.

Example 12. Role of IFN-γ on the Clinical Effect of Combination Therapy

Interferon-gamma (IFN-γ) is a pleiotropic molecule with associated antiproliferative, pro-apoptotic and antitumor mechanisms. This effector cytokine is considered to be a major effector of immunity and is a key Th1 cytokine relevant for anti-tumor immune response.

Figure 19:
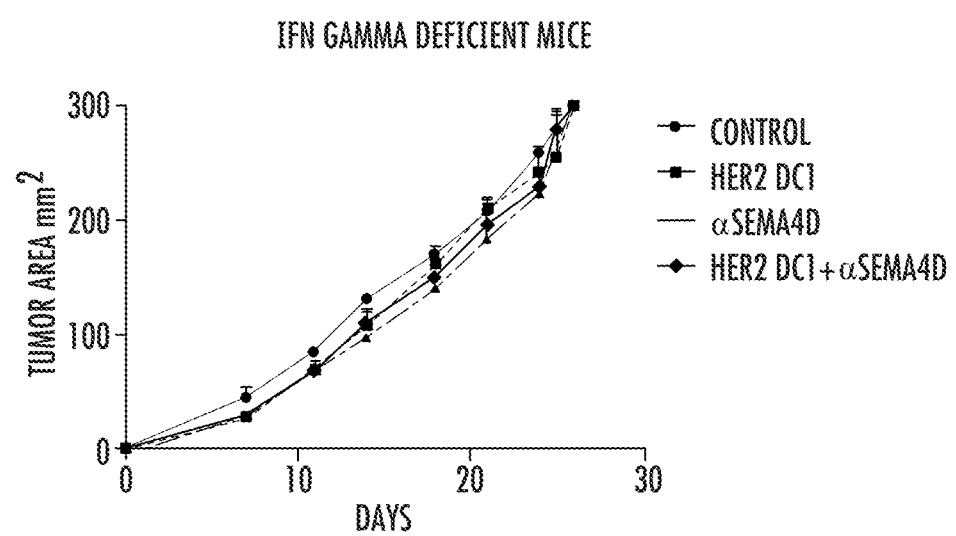
FIG. 19 shows that Interferon gamma (IFN-γ) is required for anti-tumor activity of DC1, anti-SEMA4D, and combination therapy. Mean tumor size (mm$^2$) in Balb/C IFN-γ knock out (KO) (C.129S7 (B6)-IFNg$^{tm1Ts}$/J (IFN-γ$^{KO}$, Jackson Laboratories) mice that carried tumors generated from murine Her2 TUBO breast cancer cells is shown over time following treatment with Her2DC1, anti-SEMA4D, HER2 DC1 plus anti-SEMA4D, or Control IgG.

To study the role of IFN-γ in the clinical response to the combination therapy, tumors were generated in Balb/C IFN-gamma knock out (KO) (C.129S7 (B6)-IFNg$^{Tm1Ts}$/J (IFN-γ$^{KO}$, Jackson Laboratories) mice. The mice were administered 2.5e5 TUBO cells subcutaneously on the right flank on day 0. Dendritic cells were generated, matured to DC1 and pulsed with MHC class II neu peptides. On day 7 when tumors were palpable, mice were randomized into four groups. Mice received monotherapy with either control antibody or anti-sema4D antibody (10 mg/kg/body weight) intraperitoneally until end point or 1e6/100 μl intratumoral HER2-DC1 weekly for six weeks. For combination therapy, mice received anti-sema4D antibody prior to receiving a first intratumoral HER2-DC1 injection once a week for six weeks. Tumors were measured every 2-3 days with a caliper until the endpoint. Mean tumor volume for each group is shown in FIG. 19.

The data demonstrate that anti-tumor activity of DC1, anti-SEMA and the combination requires IFN-γ for activity. These results are similar to those obtained with CD4 depletion of immunocompetent mice (FIG. 17), demonstrating that both IFN-γ and CD4 cells are necessary for anti-tumor response for ami-SEMA4D therapies.

What is claimed is:

1. An anti-cancer combination therapy comprising at least one dendritic cell pulsed with a human epidermal growth factor receptor 2 (HER2) oncodriver formulated for intratumoral administration and at least one immunoregulatory molecule inhibitor comprising an antibody or an antigen-binding fragment thereof that binds specifically to Semaphorin 4D (SEMA4D) formulated for systemic administration; and wherein administration of the combination therapy results in tumor shrinkage of injected and non-injected tumors.

2. The anti-cancer combination therapy of claim 1, wherein the oncodriver pulsed dendritic cell is activated with interleukin-12 (IL-12) prior to administration.

3. The anti-cancer combination therapy of claim 1 or claim 2, wherein the antagonist antibody that specifically binds to SEMA4D comprises pepinemab.

4. The anti-cancer combination therapy of claim 1, wherein the anti-SEMA4D antibody or antigen-binding fragment thereof blocks SEMA4D binding to its receptor.

5. The anti-cancer combination therapy of claim 1, wherein the anti-SEMA4D antibody or antigen-binding fragment thereof comprises a variable heavy chain (VH) comprising VHCDRs 1-3comprising SEQ ID NOs 5, 6, and 7, respectively and a variable light chain comprising VLCDRs 1-3 comprising SEQ ID NOs 8, 9, and 10, respectively.

6. The anti-cancer combination therapy of claim 1, wherein the anti-SEMA4D antibody or antigen-binding fragment thereof comprises a VH and a VL comprising the amino acid sequences SEQ ID NO: 3 and SEQ ID NO: 4, respectively.

* * * * *

UNITED STATES PATENT AND TRADEMARK OFFICE
CERTIFICATE OF CORRECTION

| | |
|---|---|
| PATENT NO. | : 11,660,330 B2 |
| APPLICATION NO. | : 16/906713 |
| DATED | : May 30, 2023 |
| INVENTOR(S) | : Brian Czerniecki, Krithika N. Kodumudi and Elizabeth Evans |

Page 1 of 1

It is certified that error appears in the above-identified patent and that said Letters Patent is hereby corrected as shown below:

In the Specification

Column 1, Line 12 Please insert the following heading and paragraph, immediately following the Priority paragraph:
--GRANT STATEMENT
This invention was made with Government support under Contract No. W81XWH-16-1-0385 awarded by the Department of Defense. The Government has certain rights in the invention.--

Signed and Sealed this
Third Day of February, 2026

John A. Squires
*Director of the United States Patent and Trademark Office*

SEQUENCE LISTING

```
<160> NUMBER OF SEQ ID NOS: 16

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Tyr Met His Trp Val Lys Gln Ser Pro Glu Asn Ser Leu Glu Trp Ile
        35                  40                  45

Gly Gln Ile Asn Pro Thr Thr Gly Gly Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
            85                  90                  95

Glu Asp Pro Tyr Thr Phe Gly Gly Gly Thr Lys Leu Glu Ile Lys
        100                 105                 110

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Asp Tyr
            20                  25                  30

Tyr Met His Trp Val Arg Gln Ala Pro Gly Gln Gly Leu Glu Trp Met
        35                  40                  45

Gly Gln Ile Asn Pro Thr Thr Gly Gly Ala Ser Tyr Asn Gln Lys Phe
50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Tyr Tyr Tyr Gly Arg His Phe Asp Val Trp Gly Gln Gly Thr
        100                 105                 110

Thr Val Thr Val Ser Ser
        115

<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

```
Lys Leu Leu Ile Tyr Ala Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Tyr Thr Phe Gly Gln Gly Thr Lys Leu Glu Ile Lys
            100                 105                 110

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Ser Phe Ser Asp Tyr Tyr Met His
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ile Asn Pro Thr Thr Gly Gly Ala Ser Tyr Asn Gln Lys Phe Lys
1               5                   10                  15

Gly

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Tyr Tyr Gly Arg His Phe Asp Val
1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ala Ser Gln Ser Val Asp Tyr Asp Gly Asp Ser Tyr Met Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Ala Ala Ser Asn Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Ser Asn Glu Asp Pro Tyr Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Tyr Ser Phe Ser Asp Tyr Tyr Met His
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ile Asn Pro Thr Thr Gly Gly Ala Ser Tyr Asn Gln Lys Phe Lys
1               5                   10                  15

Gly

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Tyr Tyr Gly Arg His Phe Asp Val
1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Ala Ser Gln Ser Val Asp Tyr Asp Gly Asp Ser Tyr Met Asn
1               5                   10                  15
```

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Ser Asn Glu Asp Pro Tyr Thr
1               5
```